(12) United States Patent
Hsu et al.

(10) Patent No.: US 11,937,779 B2
(45) Date of Patent: *Mar. 26, 2024

(54) DIRECTED FLUIDICS

(71) Applicant: Auris Health, Inc., Redwood City, CA (US)

(72) Inventors: Jason Joseph Hsu, Mountain View, CA (US); Ka Chun Wong, South San Francisco, CA (US); Rachel Leigh Chok, Sunnyvale, CA (US); Joshua F. DeFonzo, San Carlos, CA (US); Binh T. Nguyen, Newark, CA (US); Vivian Thalia Nguyen, Palo Alto, CA (US); Rishi Nikhil Purohit, Fremont, CA (US); Joseph A. Urban, Jr., San Carlos, CA (US)

(73) Assignee: Auris Health, Inc., Redwood City, CA (US)

( * ) Notice: Subject to any disclaimer, the term of this patent is extended or adjusted under 35 U.S.C. 154(b) by 608 days.

This patent is subject to a terminal disclaimer.

(21) Appl. No.: 17/103,044

(22) Filed: Nov. 24, 2020

(65) Prior Publication Data
US 2021/0178032 A1 Jun. 17, 2021

Related U.S. Application Data

(63) Continuation of application No. 16/212,199, filed on Dec. 6, 2018, now Pat. No. 10,850,013.
(Continued)

(51) Int. Cl.
*A61B 17/22* (2006.01)
*A61B 1/00* (2006.01)
(Continued)

(52) U.S. Cl.
CPC .......... *A61B 1/00149* (2013.01); *A61B 1/015* (2013.01); *A61B 1/2676* (2013.01);
(Continued)

(58) Field of Classification Search
CPC . A61B 17/22012; A61B 17/221; A61B 46/10; A61B 2017/00199;
(Continued)

(56) References Cited

U.S. PATENT DOCUMENTS

| 5,514,088 A | 5/1996 | Zakko |
| 5,669,876 A | 9/1997 | Schechter et al. |

(Continued)

FOREIGN PATENT DOCUMENTS

| CN | 206566279 U | 10/2017 |
| EP | 2615992 B1 | 7/2016 |

(Continued)

OTHER PUBLICATIONS

JP Office Action for appl No. 2020531507, dated Mar. 9, 2022, 6 pages.
(Continued)

*Primary Examiner* — Ryan J. Severson
(74) *Attorney, Agent, or Firm* — Chang & Hale LLP

(57) ABSTRACT

Methods and systems for administering directed fluidics during a medical procedure for removing an object are disclosed. A method includes inserting first and second medical instruments into a treatment site, providing irrigation and aspiration of the treatment site through the first and second medical instruments, determining a characteristic of one of the irrigation and the aspiration, and selecting a characteristic of the other of the irrigation and aspiration based on the determined characteristic.

20 Claims, 29 Drawing Sheets

Related U.S. Application Data

(60) Provisional application No. 62/596,711, filed on Dec. 8, 2017.

(51) Int. Cl.

| | | |
|---|---|---|
| *A61B 1/015* | (2006.01) | |
| *A61B 1/267* | (2006.01) | |
| *A61B 1/307* | (2006.01) | |
| *A61B 10/02* | (2006.01) | |
| *A61B 50/13* | (2016.01) | |
| *A61M 1/00* | (2006.01) | |
| *A61M 3/02* | (2006.01) | |
| A61B 17/00 | (2006.01) | |
| A61B 17/221 | (2006.01) | |
| A61B 17/34 | (2006.01) | |
| A61B 18/26 | (2006.01) | |
| A61B 46/10 | (2016.01) | |

(52) U.S. Cl.
CPC .......... *A61B 1/307* (2013.01); *A61B 10/0283* (2013.01); *A61B 17/22012* (2013.01); *A61B 17/2202* (2013.01); *A61B 50/13* (2016.02); *A61M 1/74* (2021.05); *A61M 1/77* (2021.05); *A61M 3/0202* (2021.05); *A61M 3/0258* (2013.01); *A61M 3/0283* (2013.01); *A61B 2017/00199* (2013.01); *A61B 2017/22079* (2013.01); *A61B 17/221* (2013.01); *A61B 17/34* (2013.01); *A61B 18/26* (2013.01); *A61B 46/10* (2016.02); *A61B 2217/005* (2013.01); *A61B 2217/007* (2013.01); *A61B 2218/002* (2013.01); *A61B 2218/007* (2013.01); *A61M 1/772* (2021.05); *A61M 2205/18* (2013.01); *A61M 2205/3331* (2013.01); *A61M 2205/3334* (2013.01)

(58) Field of Classification Search
CPC .... A61B 2017/22079; A61B 2217/005; A61B 2217/007; A61B 2218/002; A61B 2218/007

See application file for complete search history.

(56) References Cited

U.S. PATENT DOCUMENTS

| | | |
|---|---|---|
| 8,894,610 B2 | 11/2014 | MacNamara et al. |
| 9,014,851 B2 | 4/2015 | Wong et al. |
| 9,138,166 B2 | 9/2015 | Wong et al. |
| 9,173,713 B2 | 11/2015 | Hart et al. |
| 9,302,702 B1 | 4/2016 | Schepmann et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,123,843 B2 | 11/2018 | Wong et al. |
| 10,130,345 B2 | 11/2018 | Wong et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,213,264 B2 | 2/2019 | Tanner et al. |
| 10,434,660 B2 | 10/2019 | Meyer et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,517,692 B2 | 12/2019 | Eyre et al. |
| 10,524,866 B2 | 1/2020 | Srinivasan et al. |
| 10,539,478 B2 | 1/2020 | Lin et al. |
| 10,555,778 B2 | 2/2020 | Ummalaneni |
| 2004/0019358 A1 | 1/2004 | Kear |
| 2007/0232856 A1 | 10/2007 | Ueno et al. |
| 2008/0046122 A1 | 2/2008 | Manzo et al. |
| 2008/0140087 A1 | 6/2008 | Barbagli |
| 2010/0198170 A1 | 8/2010 | Umeda et al. |
| 2010/0204713 A1 | 8/2010 | Morales |
| 2010/0228266 A1 | 9/2010 | Hourtash |
| 2011/0015484 A1 | 1/2011 | Alvarez et al. |
| 2012/0071894 A1 | 3/2012 | Tanner et al. |
| 2012/0221007 A1 | 8/2012 | Batten et al. |
| 2012/0239060 A1 | 9/2012 | Orban, III |
| 2013/0123580 A1 | 5/2013 | Peters et al. |
| 2013/0165944 A1 | 6/2013 | Gal et al. |
| 2013/0209208 A1 | 8/2013 | Bailey et al. |
| 2013/0218005 A1 | 8/2013 | Desai et al. |
| 2014/0142591 A1 | 5/2014 | Alvarez et al. |
| 2014/0257333 A1 | 9/2014 | Blumenkranz |
| 2014/0276392 A1 | 9/2014 | Wong et al. |
| 2014/0276934 A1 | 9/2014 | Balaji et al. |
| 2014/0276937 A1 | 9/2014 | Wong et al. |
| 2014/0276938 A1 | 9/2014 | Hsu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0119638 A1 | 4/2015 | Yu et al. |
| 2015/0164594 A1 | 6/2015 | Romo et al. |
| 2015/0164596 A1 | 6/2015 | Romo et al. |
| 2015/0305759 A1 | 10/2015 | George et al. |
| 2015/0311838 A1 | 10/2015 | Moule et al. |
| 2015/0327939 A1 | 11/2015 | Kokish et al. |
| 2015/0335480 A1 | 11/2015 | Alvarez et al. |
| 2016/0001038 A1 | 1/2016 | Romo et al. |
| 2016/0007881 A1 | 1/2016 | Wong et al. |
| 2016/0166320 A1 | 6/2016 | Ciulla et al. |
| 2016/0270804 A1 | 9/2016 | Honda et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0100199 A1 | 4/2017 | Yu et al. |
| 2017/0106904 A1 | 4/2017 | Hanson et al. |
| 2017/0119413 A1 | 5/2017 | Romo |
| 2017/0119481 A1 | 5/2017 | Romo et al. |
| 2017/0135718 A1 | 5/2017 | Lyons |
| 2017/0165011 A1 | 6/2017 | Bovay et al. |
| 2017/0172673 A1 | 6/2017 | Yu et al. |
| 2017/0196576 A1 | 7/2017 | Long et al. |
| 2017/0202627 A1 | 7/2017 | Sramek et al. |
| 2017/0209073 A1 | 7/2017 | Sramek et al. |
| 2017/0215897 A1 | 8/2017 | Fan |
| 2017/0215899 A1 | 8/2017 | Harrah et al. |
| 2017/0215964 A1 | 8/2017 | Harrah et al. |
| 2017/0215965 A1 | 8/2017 | Harrah et al. |
| 2017/0231647 A1 | 8/2017 | Saunders et al. |
| 2017/0245854 A1 | 8/2017 | Zemlok et al. |
| 2017/0290631 A1 | 10/2017 | Lee et al. |
| 2017/0326337 A1 | 11/2017 | Romoscanu et al. |

(56) References Cited

U.S. PATENT DOCUMENTS

| | | |
|---|---|---|
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0056044 A1 | 3/2018 | Choi et al. |
| 2018/0169671 A1 | 6/2018 | Winter et al. |
| 2018/0177383 A1 | 6/2018 | Noonan et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0022767 A1 | 1/2020 | Hill et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0060516 A1 | 2/2020 | Baez, Jr. |

FOREIGN PATENT DOCUMENTS

| | | |
|---|---|---|
| WO | 2017053698 A1 | 3/2017 |
| WO | 2017075574 A1 | 5/2017 |

OTHER PUBLICATIONS

Preliminary Rejection for KR Appl No. 20207014162, dated Dec. 30, 2021, 9 pages.

EP Search Report for Appl. No. 18885391.5, dated Apr. 21, 2023, 4 pages.

EP Search report for appl No. 18885391, dated Aug. 25, 2021, 12 pages.

CN Office Action for Appl. No. 201880079048.2, dated Apr. 25, 2022, 3 pages.

Seach Report for Appl. No. 201880079048.2, dated Apr. 25, 2022, 2 pages.

AU Examination Report for Appl. No. 2018378808, dated Nov. 2, 2023, 3 pages.

DIRECTED FLUIDICS

INCORPORATION BY REFERENCE TO ANY PRIORITY APPLICATION(S)

This application is a continuation of U.S. application Ser. No. 16/212,199, filed Dec. 6, 2018, which claims priority to U.S. Provisional Application No. 62/596,711, filed Dec. 8, 2017, each of which is incorporated herein by reference. Any and all applications for which a foreign or domestic priority claim is identified in the Application Data Sheet as filed with the present application are hereby incorporated by reference under 37 CFR 1.57.

TECHNICAL FIELD

The systems and methods disclosed herein are directed to medical robotics, and more particularly, to robotic medical systems and methods employing directed fluidics during procedures for removal of an object from a patient.

BACKGROUND

Every year, physicians perform procedures to remove urinary stones from patients' urinary tracts. Urinary stones may include kidney stones, found in the kidneys and ureters, as well as bladder stones, found in the bladder. Such urinary stones may form as a result of concentrated minerals and may cause significant abdominal pain once they reach a size sufficient to impede urine flow through the ureter or urethra. Such stones may be formed from calcium, magnesium, ammonia, uric acid, cysteine, or other compounds.

To remove urinary stones from the bladder and ureter, physicians generally use a ureteroscope inserted into the urinary tract through the urethra. Typically, a ureteroscope includes a scope at its distal end to enable visualization of the urinary tract. The procedure may also utilize a lithotomy mechanism to capture or break apart the urinary stones. During the ureteroscopy procedure, one physician may control the position of the ureteroscope and the other physician may control the lithotomy mechanism. To remove large kidney stones from the kidneys, physicians generally use a percutaneous nephrolithotomy (PCNL) technique that includes inserting a nephroscope through the skin to break up and remove the kidney stones.

SUMMARY

This disclosure relates to systems and techniques for removing an object from a treatment site of a patient, and in particular to methods and systems that employ directed fluidics during an object removal procedure. "Directed fluidics" can refer to methods and systems for providing irrigation and aspiration (e.g., inflow and outflow of fluid) that improve or facilitate an object removal procedure. Directed fluidics can include setting, controlling, or adjusting characteristics of irrigation and/or aspiration to achieve advantageous, beneficial, or desirable fluid flows through a treatment site.

In a first aspect, a method of administering fluidics during a medical procedure, includes: inserting a first medical instrument into a treatment site, the first medical instrument comprising a first fluid channel and a second fluid channel; providing irrigation into the treatment site through the first fluid channel of the first medical instrument; providing aspiration from the treatment site through the second fluid channel of the first medical instrument; determining a characteristic of one of the irrigation and the aspiration; and selecting a characteristic of the other of the irrigation and aspiration based on the determined characteristic.

The method can include one or more of the following features, in any combination: (a) wherein inserting the first medical instrument into the treatment site comprises advancing the first medical instrument percutaneously into the treatment site; (b) wherein inserting the first medical instrument into the treatment site comprises advancing the first medical instrument through a lumen of a patient into the treatment site; (c) inserting a second medical instrument into the treatment site through a lumen of the patient; (d) percutaneously inserting a second medical instrument into the treatment site; (e) wherein the determined characteristic comprises at least one of an instantaneous flow rate and an average flow rate over a period of time; (f) wherein the selected characteristic comprises at least one of an instantaneous flow rate and an average flow rate over a period of time; (g) wherein the selected characteristic substantially matches the determined characteristic; (h) determining a characteristic of the treatment site, and when the determined characteristic of the treatment site exceeds a threshold value, at least one of: reducing irrigation into the treatment site, increasing aspiration from the treatment site, and providing an alert; (i) wherein the determined characteristic of the treatment site comprises one of a volume of fluid within the treatment site and an internal pressure of the treatment site; (j) moving a distal tip of the first medical instrument in a sweeping motion while providing irrigation or aspiration; (k) wherein at least one of the first medical instrument and the second medical instrument is robotically controlled; (l) performing lithotripsy on an object within the treatment site to break the object into fragments, and aspirating the fragments through the second fluid channel of the first medical instrument; (m) wherein lithotripsy is performed with a second medical instrument; (n) wherein the first medical instrument comprises a steerable medical instrument comprising an articulable distal end; (o) contacting an articulable distal end of the first medical instrument to an object within the treatment site, and providing aspiration through the second fluid channel to hold the object to the articulable distal end; (p) wherein the articulable distal end comprises a pocket configured to hold the object; (q) performing lithotripsy while the object is held in the pocket; (r) moving the first medical instrument to reposition the object within the treatment site; (s) performing lithotripsy on an object within the treatment site to break the object into fragments, and aspirating, during the lithotripsy, through the second fluid channel to remove dust created by the lithotripsy; (t) wherein the additional first fluid channel includes a fluid orifice that directs fluid away from the second medical instrument; (u) wherein irrigation and aspiration are provided at the same time; and/or (v) wherein irrigation and aspiration are not provided at the same time.

In another aspect, a system for performing a medical procedure can include: a first medical instrument configured to be inserted into a treatment site, the first instrument including a first fluid channel and a second fluid channel; a vacuum connected to one of the first fluid channel and the second fluid channel and configured to apply a negative pressure to provide aspiration from the treatment site; a pump coupled to an irrigation source and the other of the first fluid channel and the second fluid channel, the pump configured to provide irrigation to the treatment site; and a fluidics control system coupled to the vacuum and the pump, the fluidics control system comprising one or more processors configured to: determine a characteristic of one of the irrigation and the aspiration, and control a characteristic of at least one of the pump or the vacuum based on the determined characteristic.

The system can include one or more of the following features in any combination: (a) wherein the first medical instrument is configured to be inserted through a lumen of a patient into the treatment site; (b) wherein the first medical instrument is configured to be inserted percutaneously into the treatment site; (c) wherein further comprising a second medical instrument is configured to be inserted through a lumen of a patient into the treatment site; (d) comprising a second medical instrument that is configured to be inserted percutaneously into the treatment site; (e) wherein the first medical instrument further comprises a flow rate sensor positioned in the first fluid channel, and wherein an output of the flow rate sensor is connected to the fluidics control system; (f) wherein the second first medical instrument further comprises a flow rate sensor positioned in the second fluid channel, and wherein an output of the flow rate sensor is connected to the fluidics control system; (g) wherein the first medical instrument further comprises a pressure sensor disposed to measure an internal pressure of the treatment site, an output of the pressure sensor connected to the fluidics control system, and wherein the one or more processors are further configured to control at least one of the pump or the vacuum to adjust at least one of the aspiration and the irrigation based on the measured internal pressure of the treatment site; (h) a second medical instrument configured to be inserted into the treatment site, wherein the second medical instrument further comprises a pressure sensor disposed to measure an internal pressure of the treatment site, an output of the pressure sensor connected to the fluidics control system, and wherein the one or more processors are further configured to control at least one of the pump or the vacuum to adjust at least one of the aspiration and irrigation based on the measured internal pressure of the treatment site; and/or (i) wherein the first medical instrument comprises an articulable distal end.

In another aspect, a medical device can include: an articulable elongate body extending along an axis to a distal end; a first fluid channel extending along the axis, the first fluid channel terminating in a first fluid orifice formed in a distal face of the distal end; and at least one additional fluid channel formed through the elongate body, the at least one additional fluid channel terminating in at least one additional fluid exit orifice formed in a radial surface of the elongate body proximal the distal end.

The medical device can include one or more of the following features in any combination: (a) a pocket formed in the distal face; (b) wherein the pocket is configured to at least partially receive an object to be removed during a medical procedure; (c) wherein the at least one additional channel annularly surrounds the first fluid channel; (d) wherein the at least one additional fluid orifice comprises additional fluid orifices positioned around the axis; (e) wherein the at least one additional channel comprises additional channels positioned radially around the first fluid channel; (f) wherein each of the four additional fluid channels terminates at an additional fluid orifice positioned radially around the axis; and/or (g) at least one pull wire for articulating the elongate body.

In another aspect, a non-transitory computer readable storage medium can include stored thereon instructions that, when executed, cause a processor of a device to at least: determine a characteristic of at least one of irrigation into a treatment site through a first channel of a first medical instrument and an aspiration from the treatment site through a second channel of the first medical instrument; and select a characteristic of at least one of the irrigation and the aspiration based on the determined characteristic.

The non-transitory computer readable storage medium can include one or more of the following features in any combination: (a) wherein the determined characteristic comprises at least one of an instantaneous flow rate and an average flow rate over a period of time; (b) wherein the selected characteristic comprises at least one of an instantaneous flow rate and an average flow rate over a period of time; (c) wherein the selected characteristic substantially matches the determined characteristic; (d) wherein the instructions, when executed further cause the processor to determine a characteristic of the treatment site, and when the determined characteristic of the treatment site exceeds a threshold value, at least one of: reduce irrigation into the treatment site, increase aspiration from the treatment site, and provide an alert; (e) wherein the determined characteristic of the treatment site comprises one of a volume of fluid within the treatment site and an internal pressure of the treatment site; (f) wherein the instructions, when executed further cause the processor to: perform lithotripsy with a second medical instrument on an object within the treatment site to break the object into fragments, and aspirate the fragments through the second fluid channel of the second first medical instrument; (g) wherein the instructions, when executed further cause the processor to: perform lithotripsy with a second medical instrument on an object within the treatment site to break the object into fragments, and aspirate, during the lithotripsy, through the second fluid channel of the second first medical instrument to remove dust created by the lithotripsy; (h) wherein the instructions, when executed further cause the processor to provide irrigation and aspiration at the same time; and/or (i) wherein irrigation and aspiration are not provided at the same time.

In another aspect, a method of administering fluidics during the removal of an object from a patient can include: advancing a first medical instrument through a lumen of a patient toward a treatment site containing an object to be removed, the first medical instrument comprising a first fluid channel for providing irrigation through a first aperture positioned on a remotely articulable distal tip, the first aperture configured to provide irrigation in a first fluid flow direction; inserting a second medical instrument percutaneously into the treatment site, the second medical instrument comprising a second fluid channel for providing aspiration through a second aperture of the second fluid channel; providing irrigation into the treatment site with the first medical instrument through the first aperture; providing aspiration from the treatment site through the second aperture of the second fluid channel of the second medical instrument; and remotely manipulating the distal tip of the first medical instrument such that the first fluid direction is oriented towards the second aperture.

The method can include one or more of the following features in any combination: (a) determining the position of the second aperture within the treatment site, and wherein manipulating the distal tip comprises automatically manipulating the distal tip based on the determined position of the second aperture within the treatment site; (b) wherein a nephroscope comprises the second medical instrument and a lithotripter, and wherein the method further comprises: contacting the lithotripter to the object, performing lithotripsy to break the object into fragments, and aspirating the fragments with the suction tube; and/or (c) moving a distal tip of the first medical instrument in a sweeping motion while providing irrigation through the first medical instrument.

Although this disclosure is largely described with respect to example use cases of ureteroscopy, percutaneous nephrolithotomy (PCNL), and the removal of urinary stones and stone fragments, this disclosure may be equally applicable to other surgical/medical operations concerned with the removal of objects from various treatment sites of the patient, including any object that can be safely removed via a patient cavity (e.g., the esophagus, ureter, intestine, etc.) or via percutaneous access, such as gallbladder stone removal or lung (pulmonary/transthoracic) tumor biopsy.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
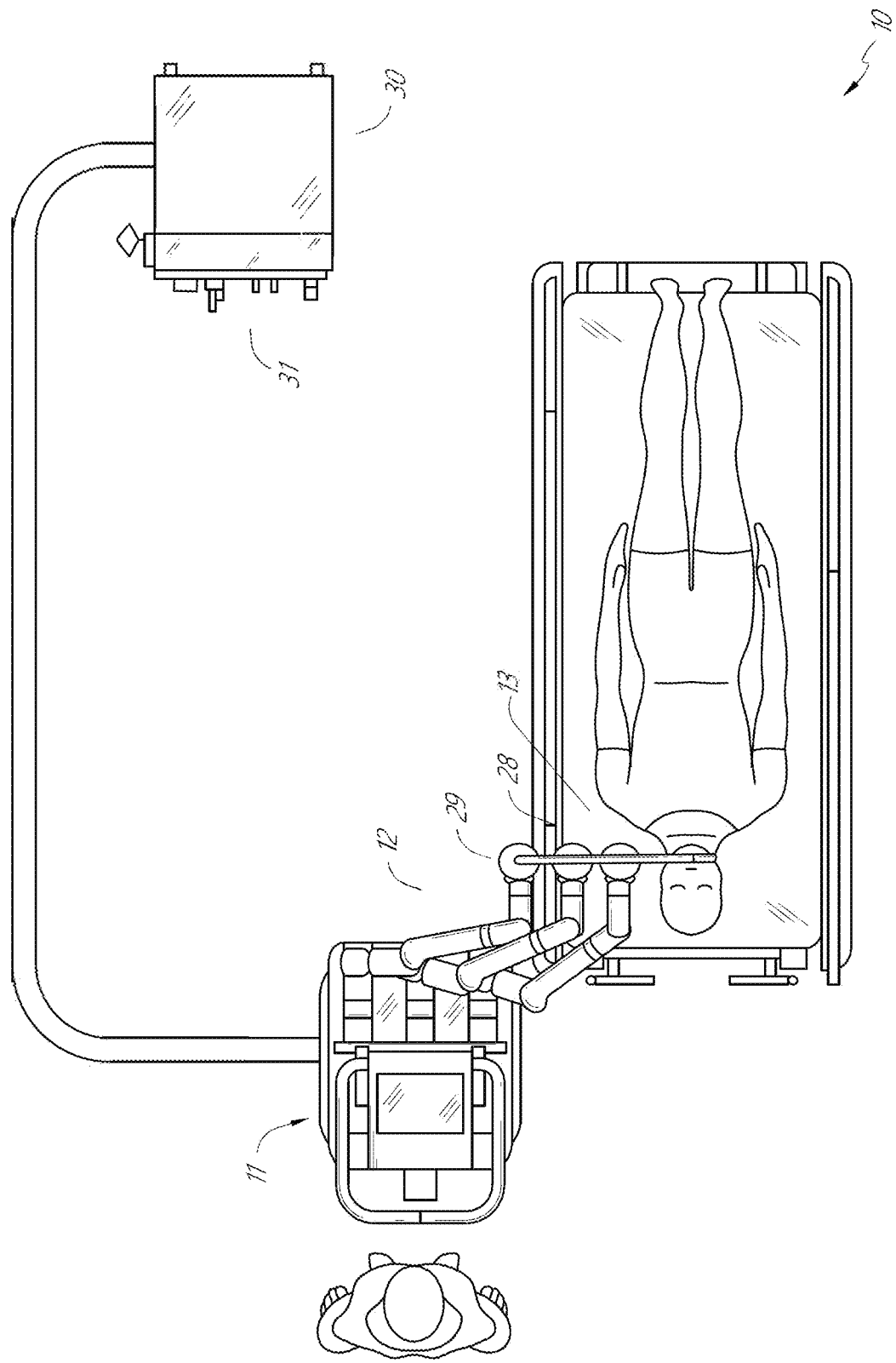
FIG. 1 illustrates an embodiment of a cart-based robotic system arranged for diagnostic and/or therapeutic bronchoscopy procedure(s).
Figure 2:
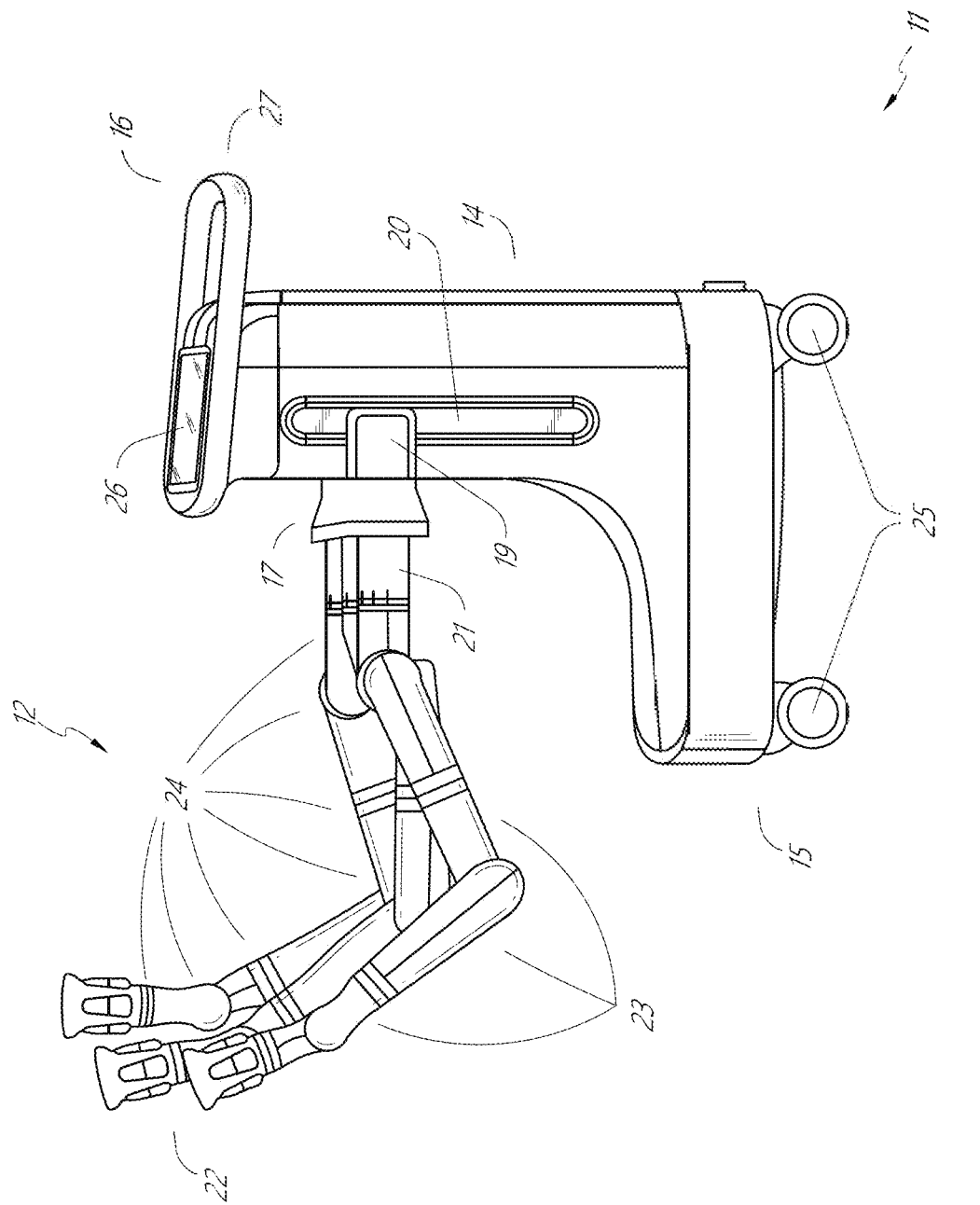
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or repositioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
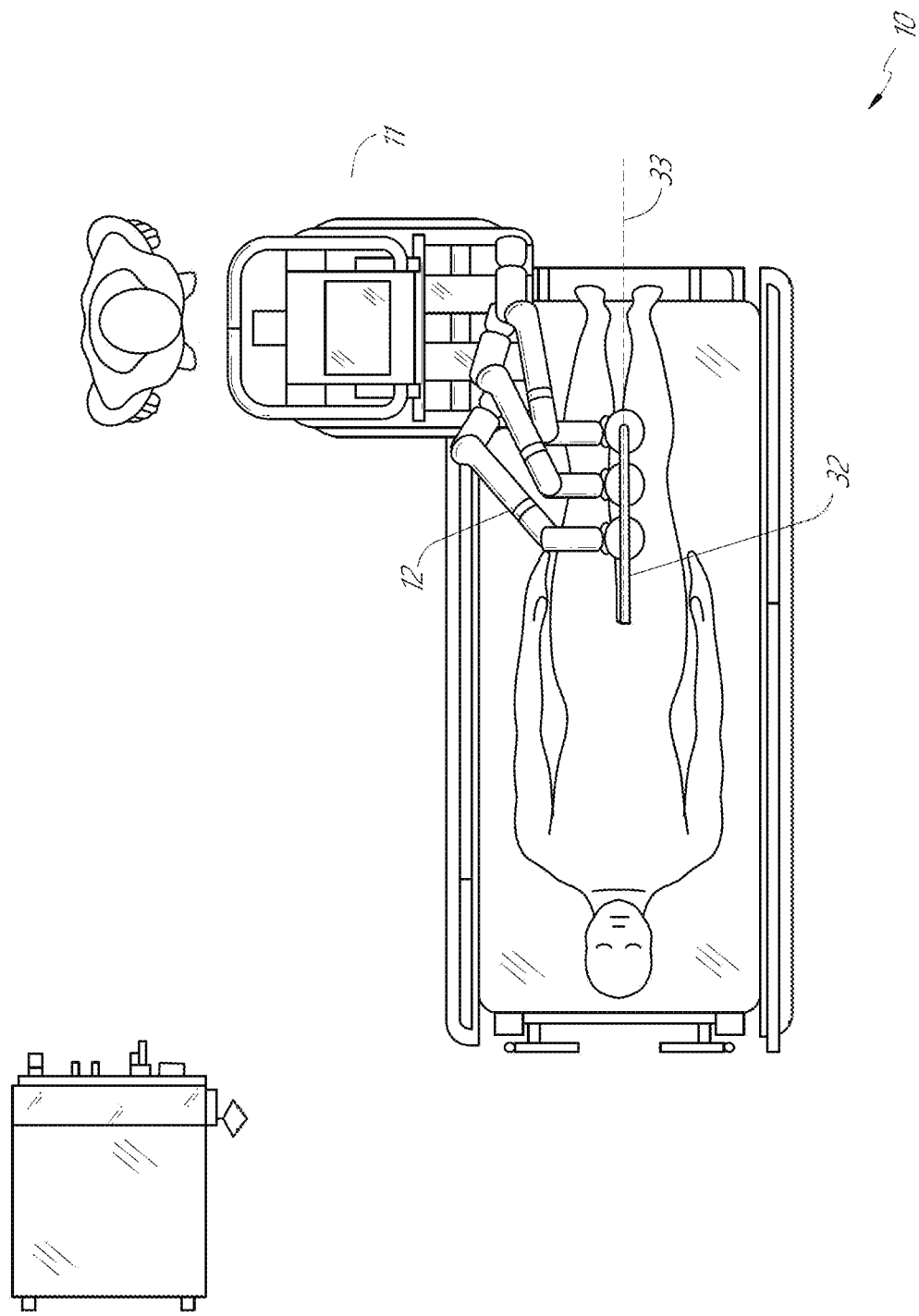
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
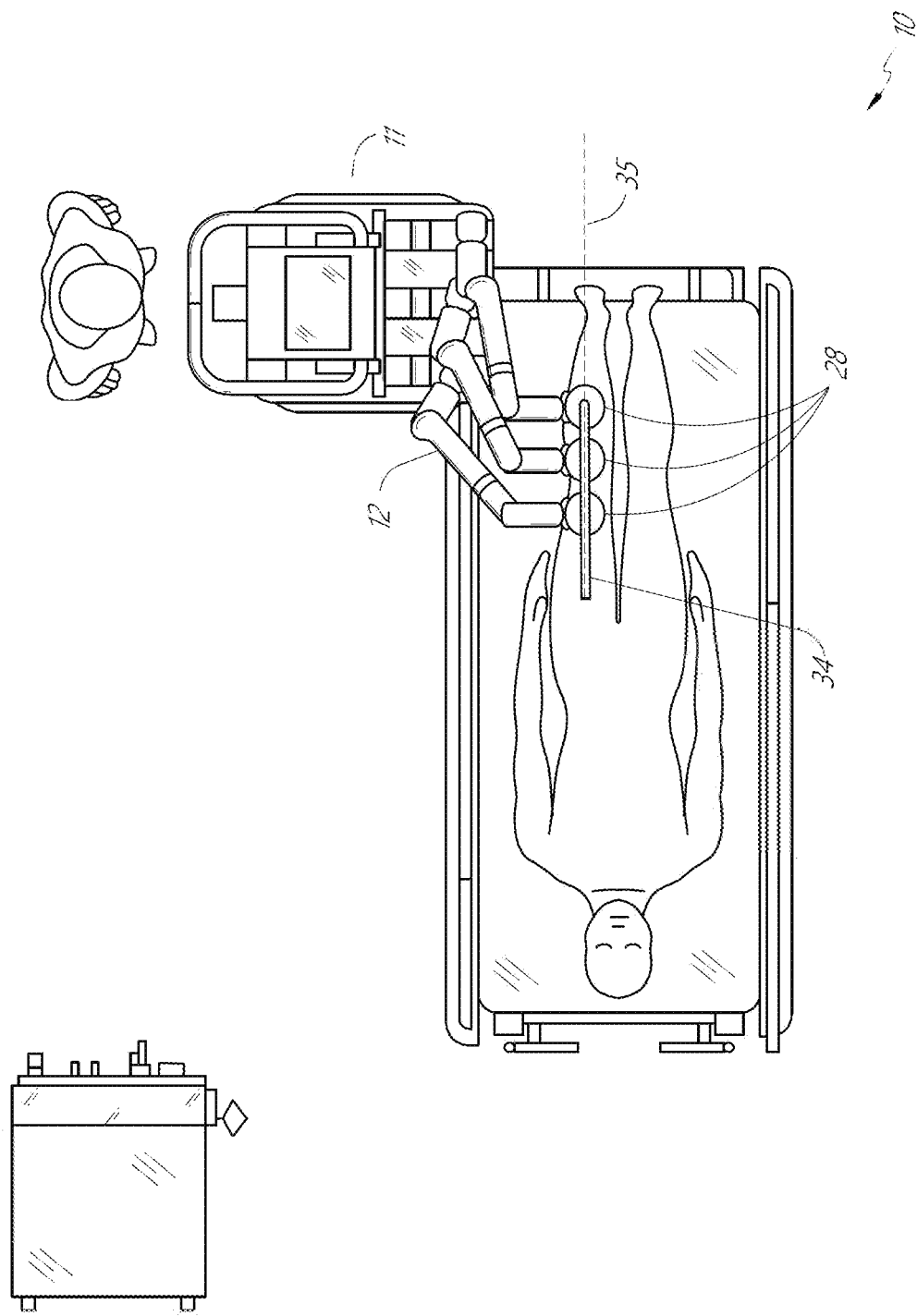
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
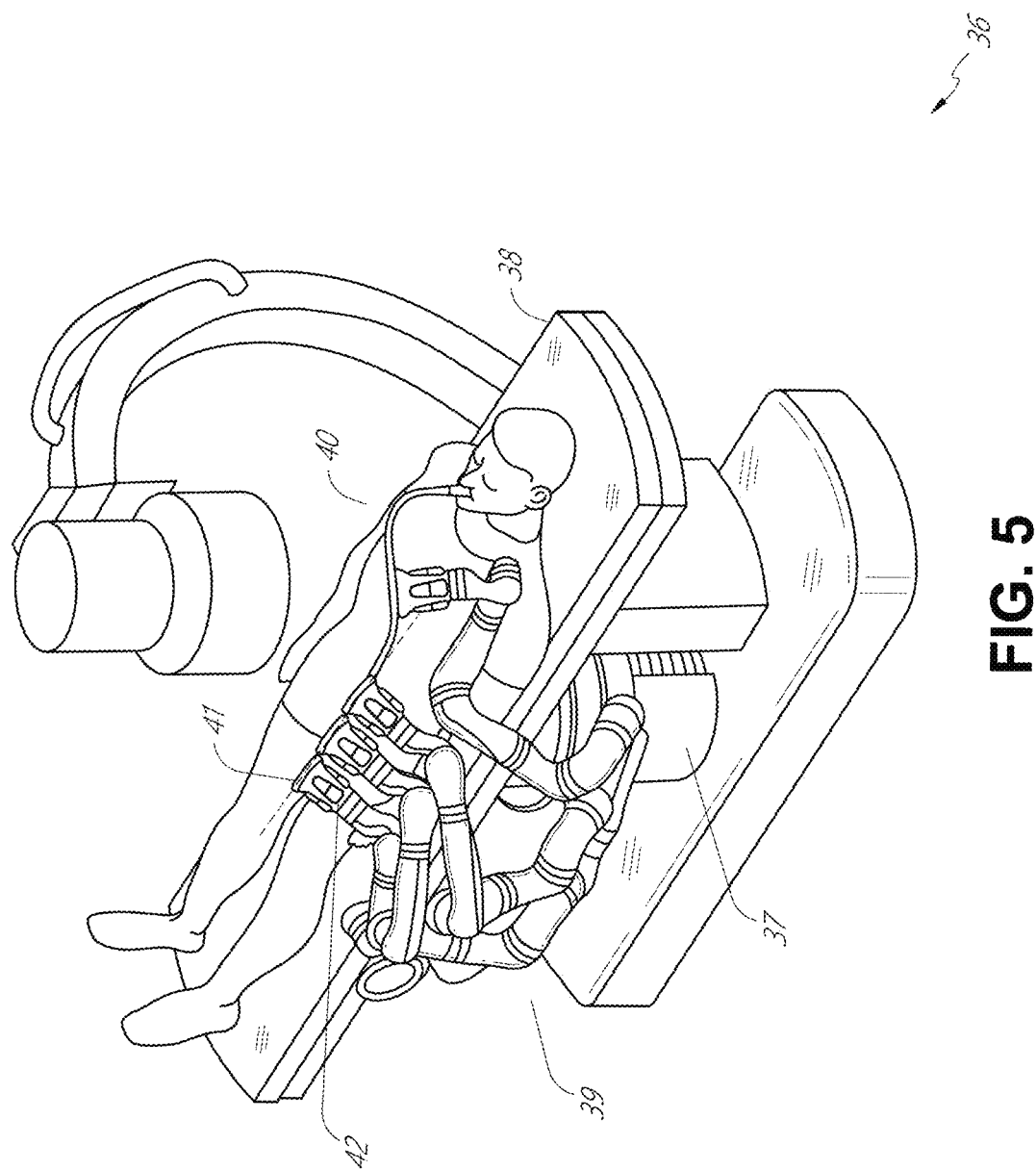
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
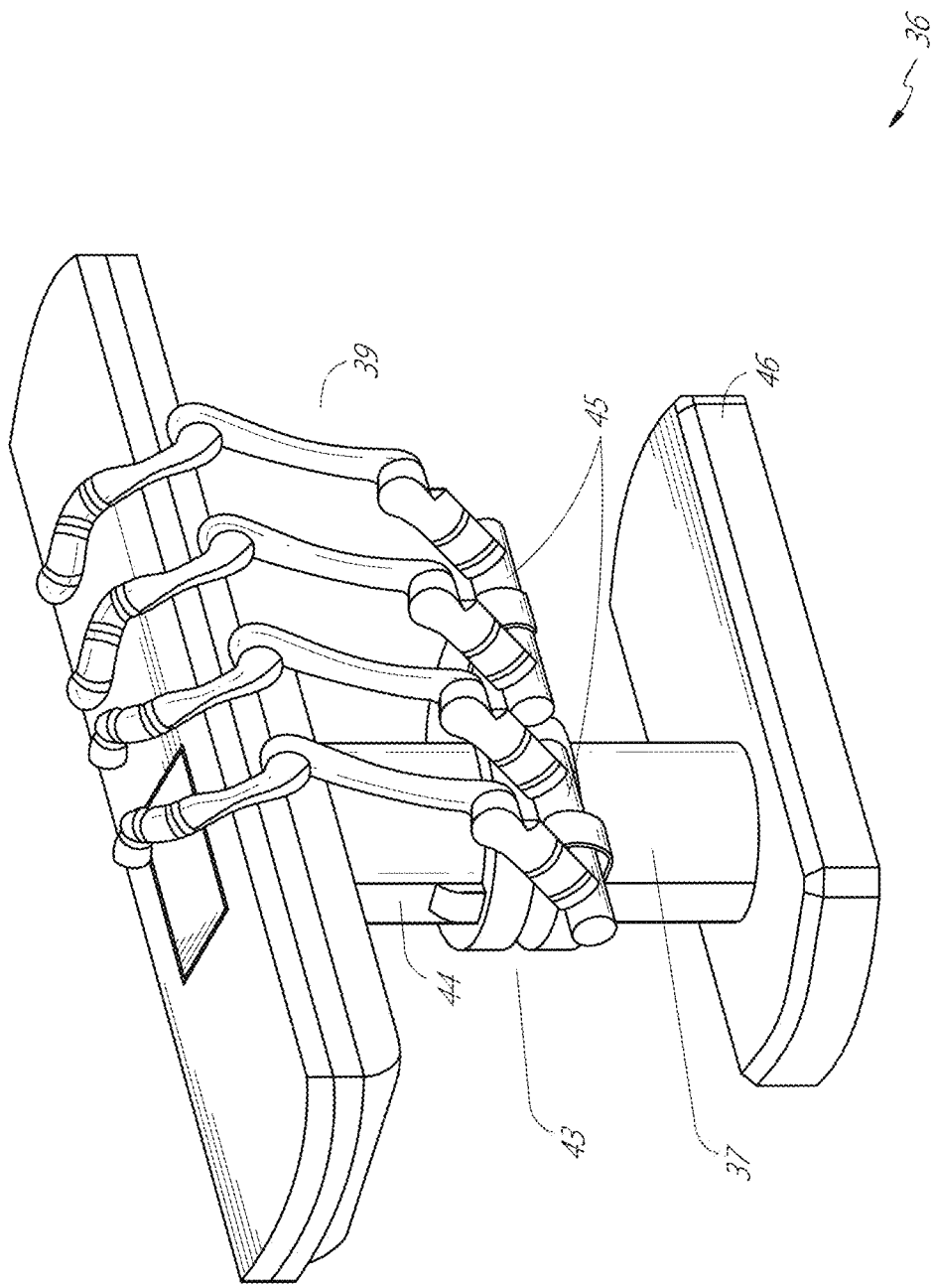
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
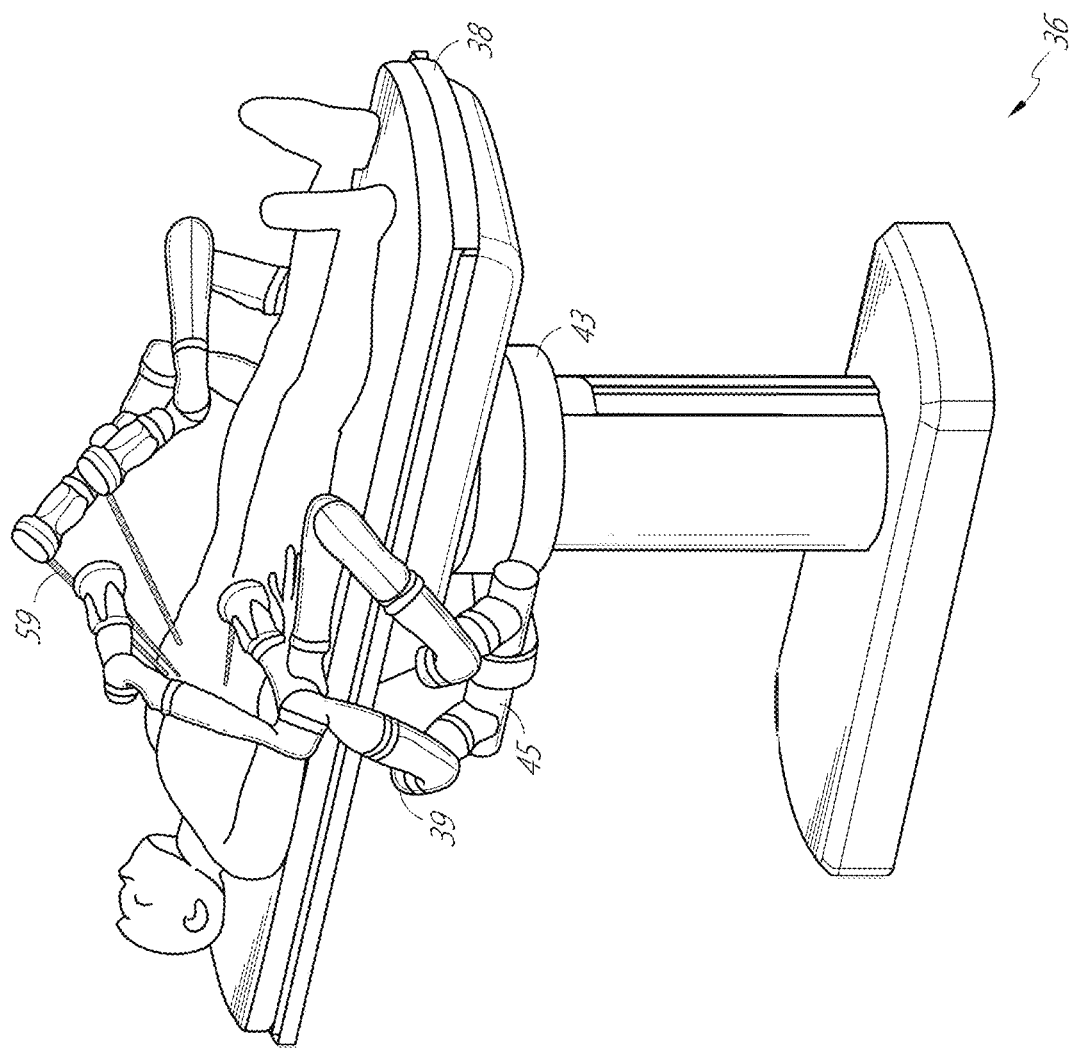
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
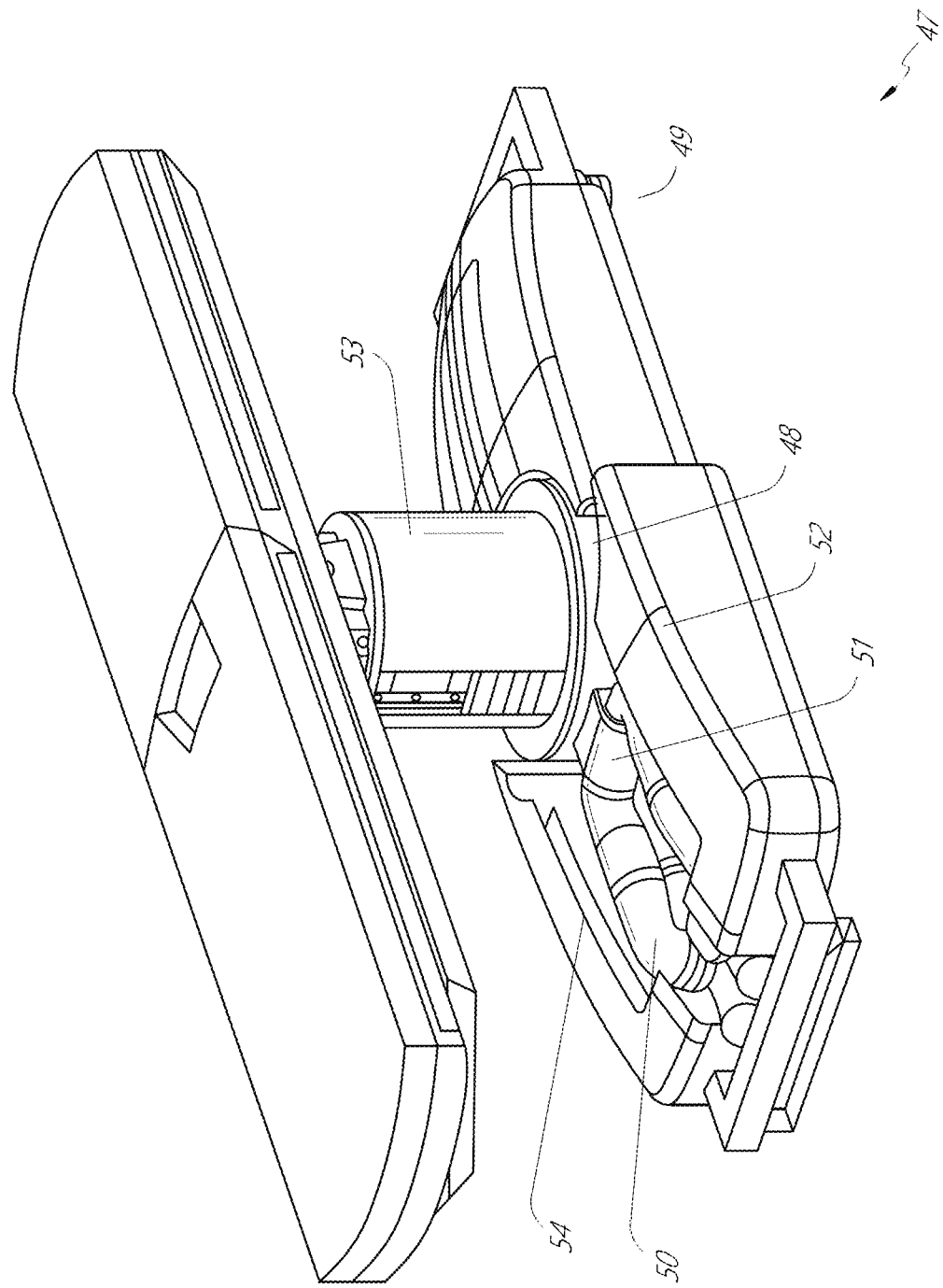
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
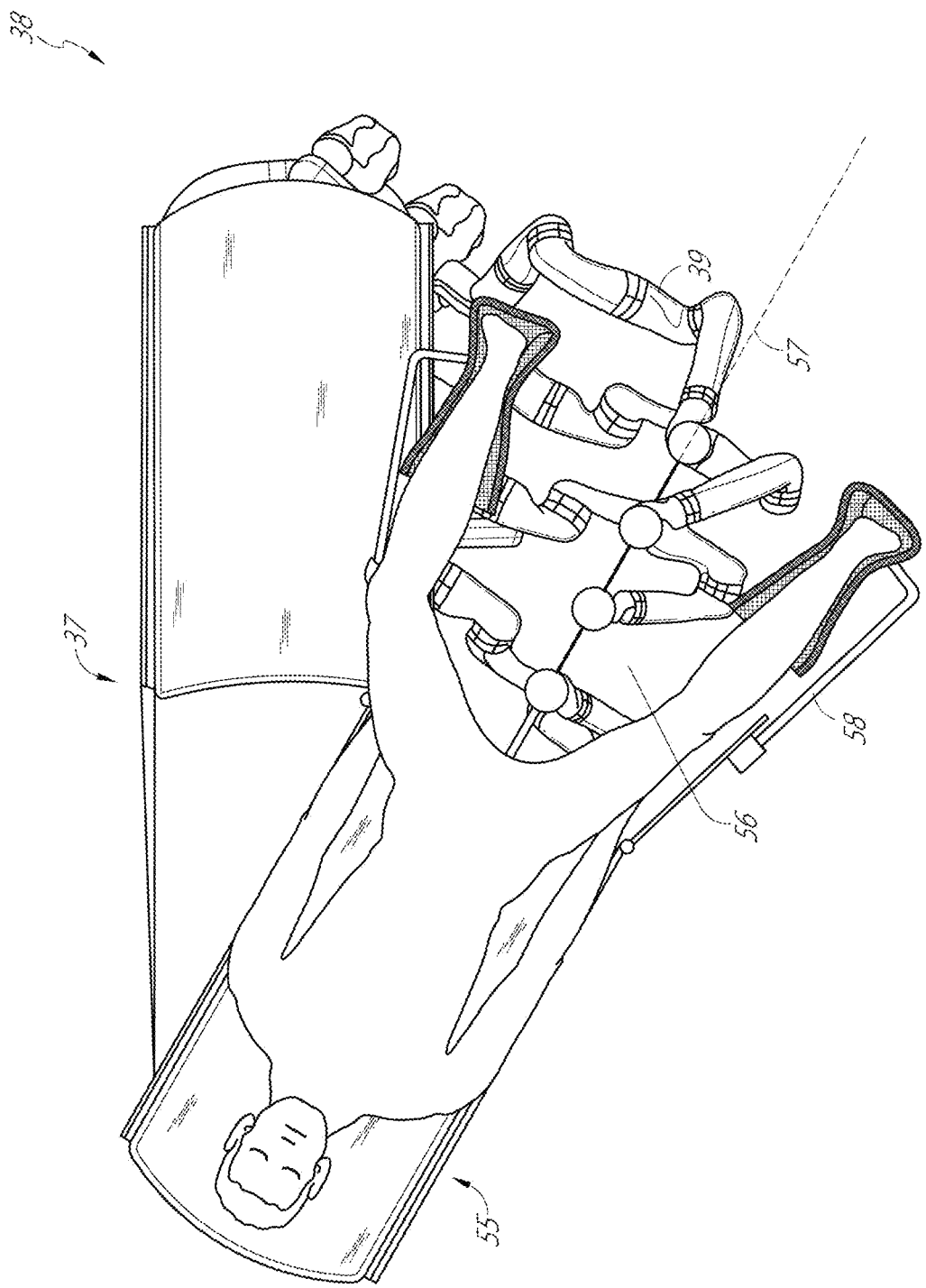
FIG. 8 illustrates an embodiment of a table-based robotic system configured for a ureteroscopy procedure.

FIG. 8 illustrates an embodiment of a robotically-enabled table-based system configured for a ureteroscopy procedure. In ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
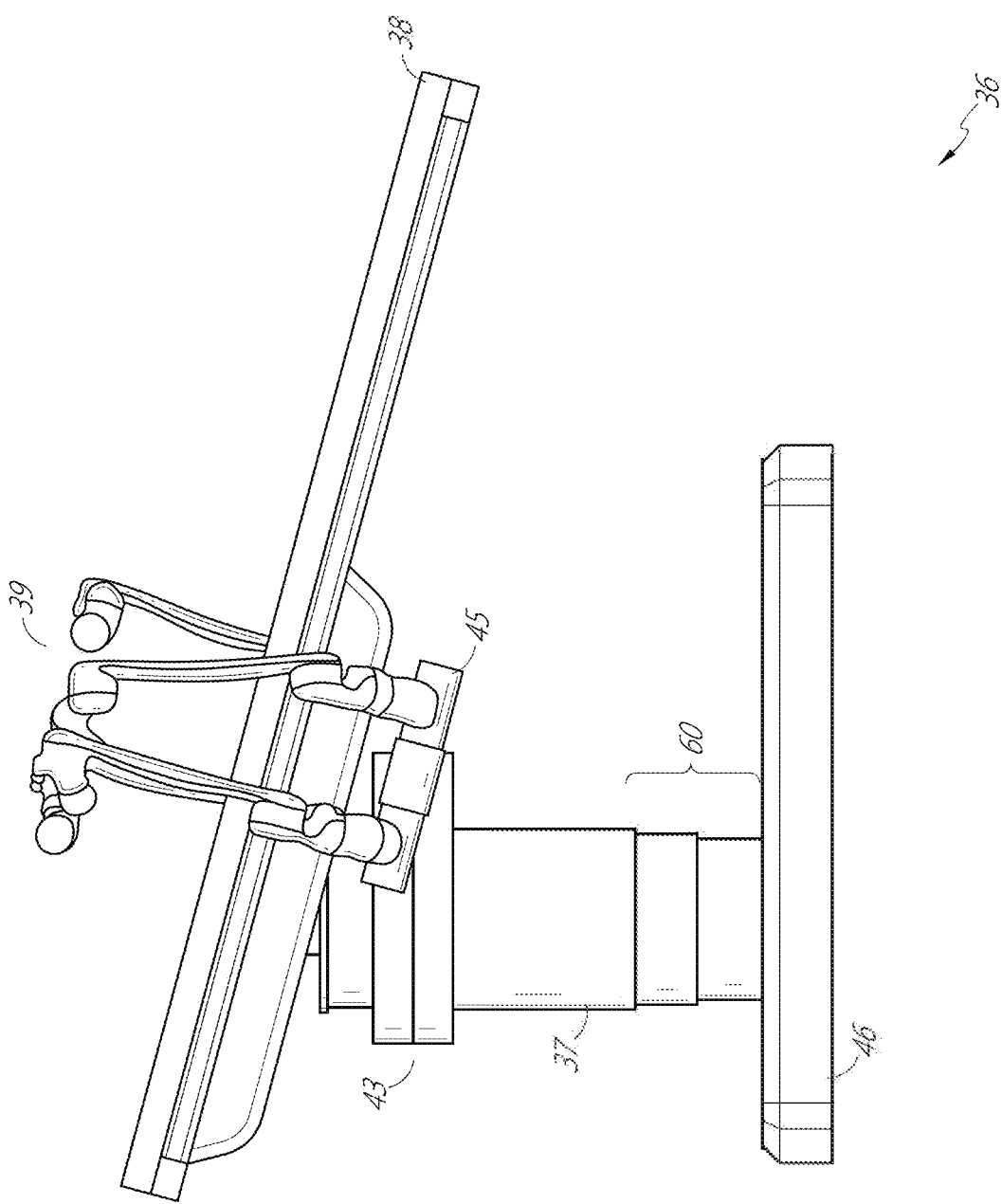
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
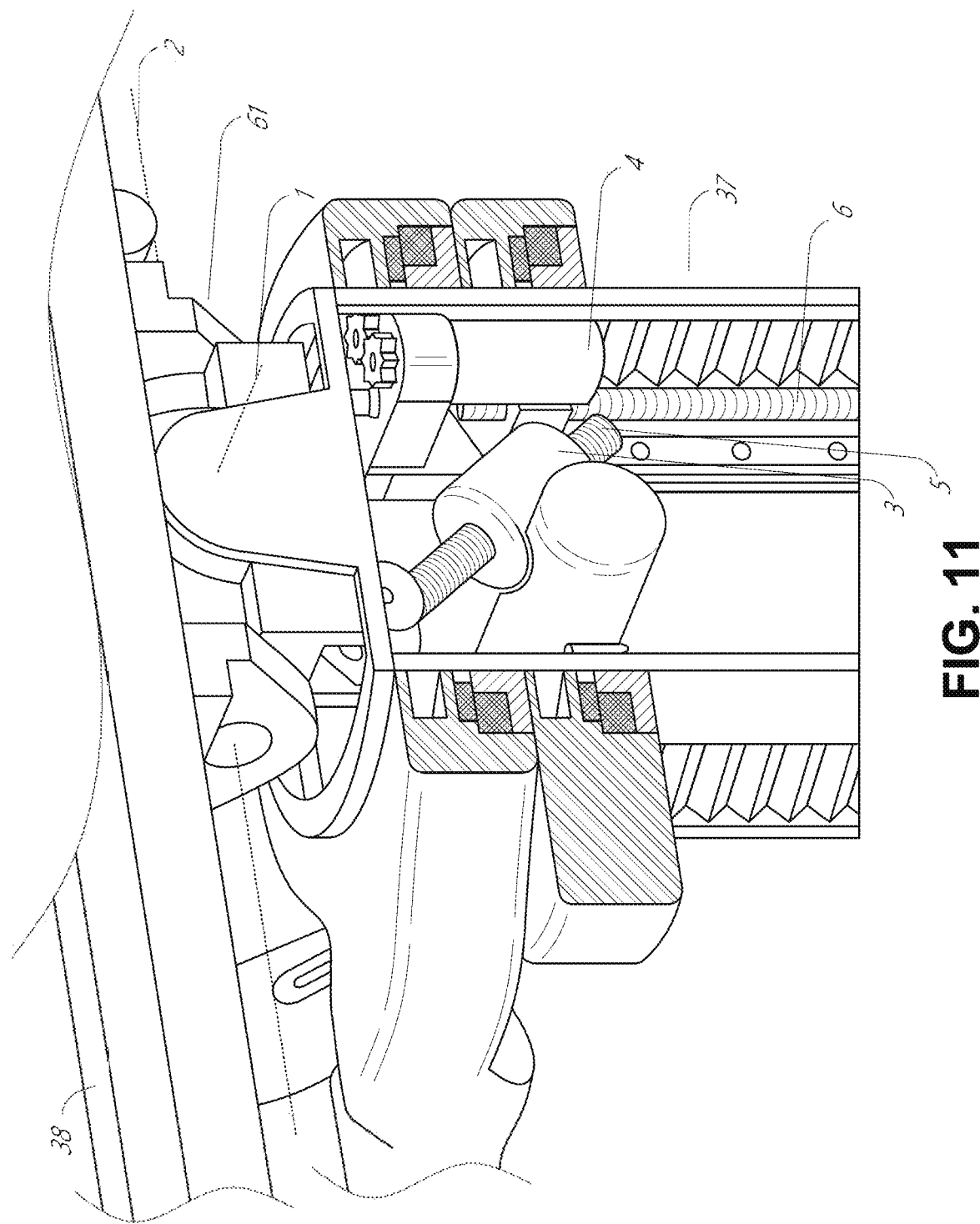
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
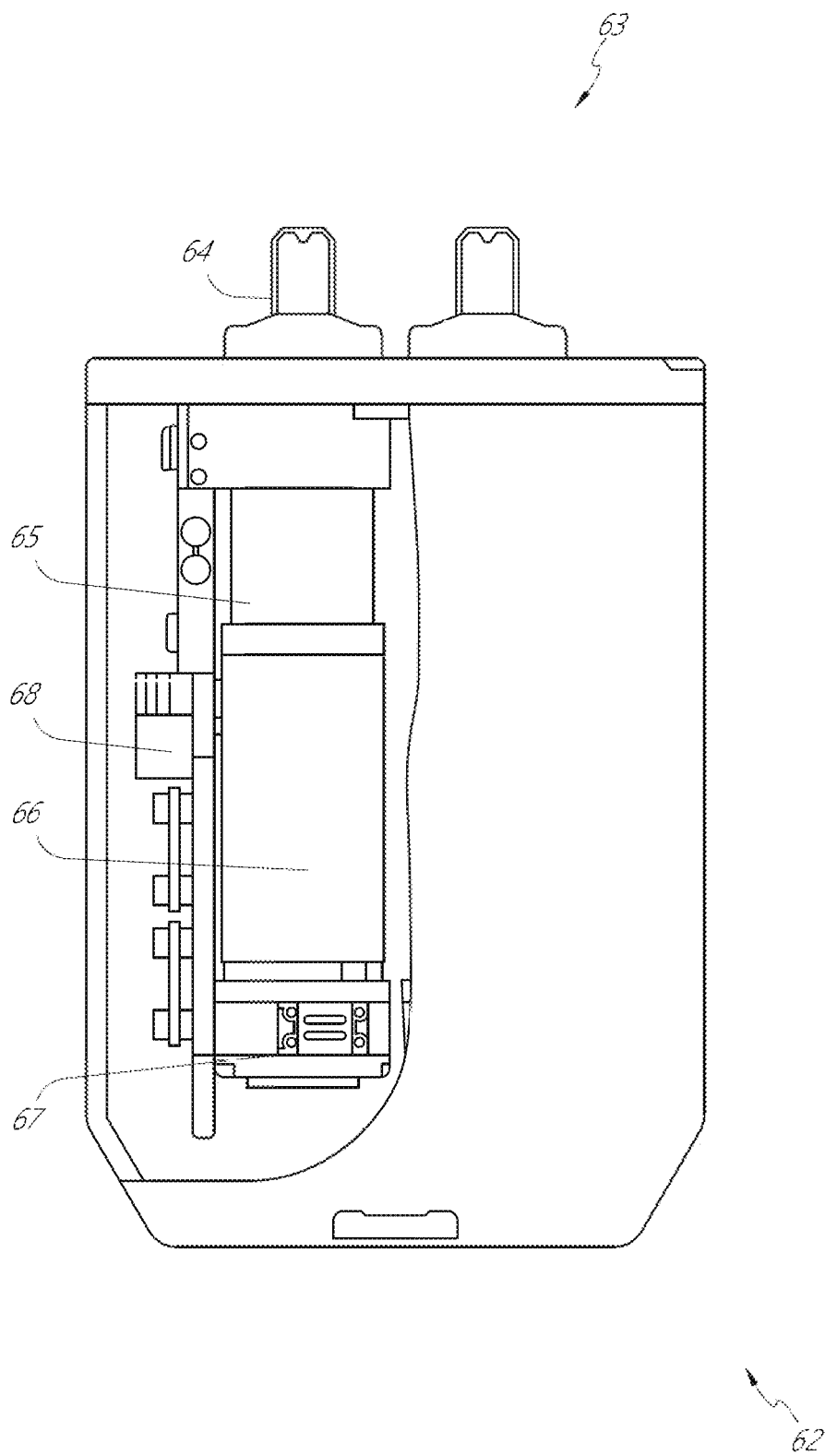
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
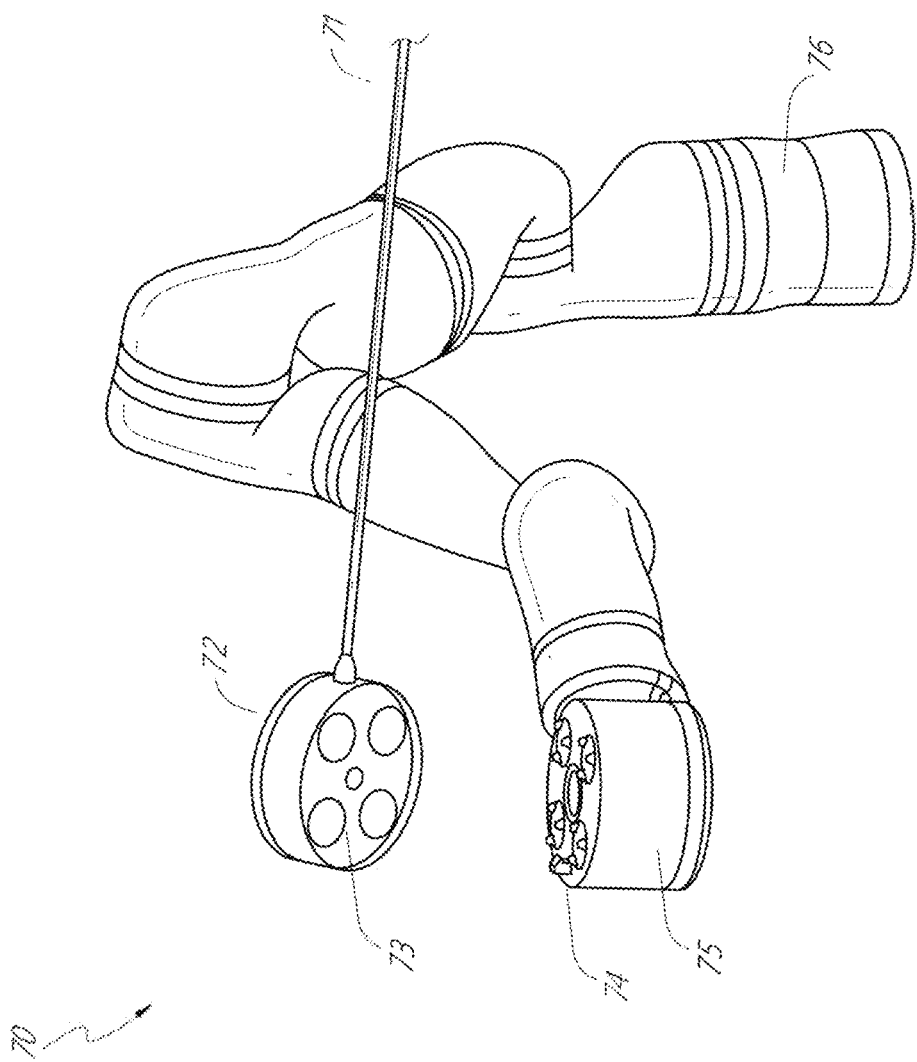
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
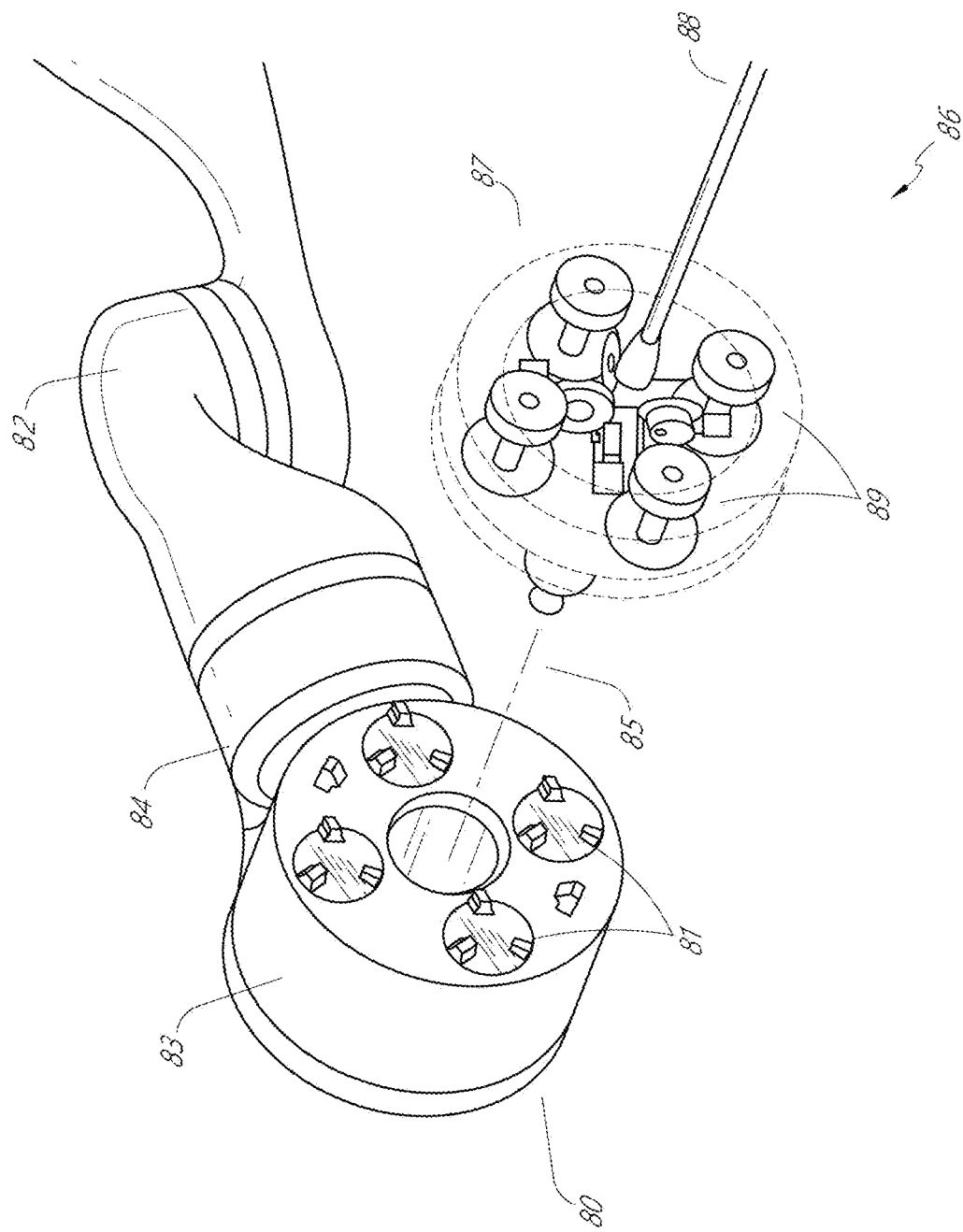
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
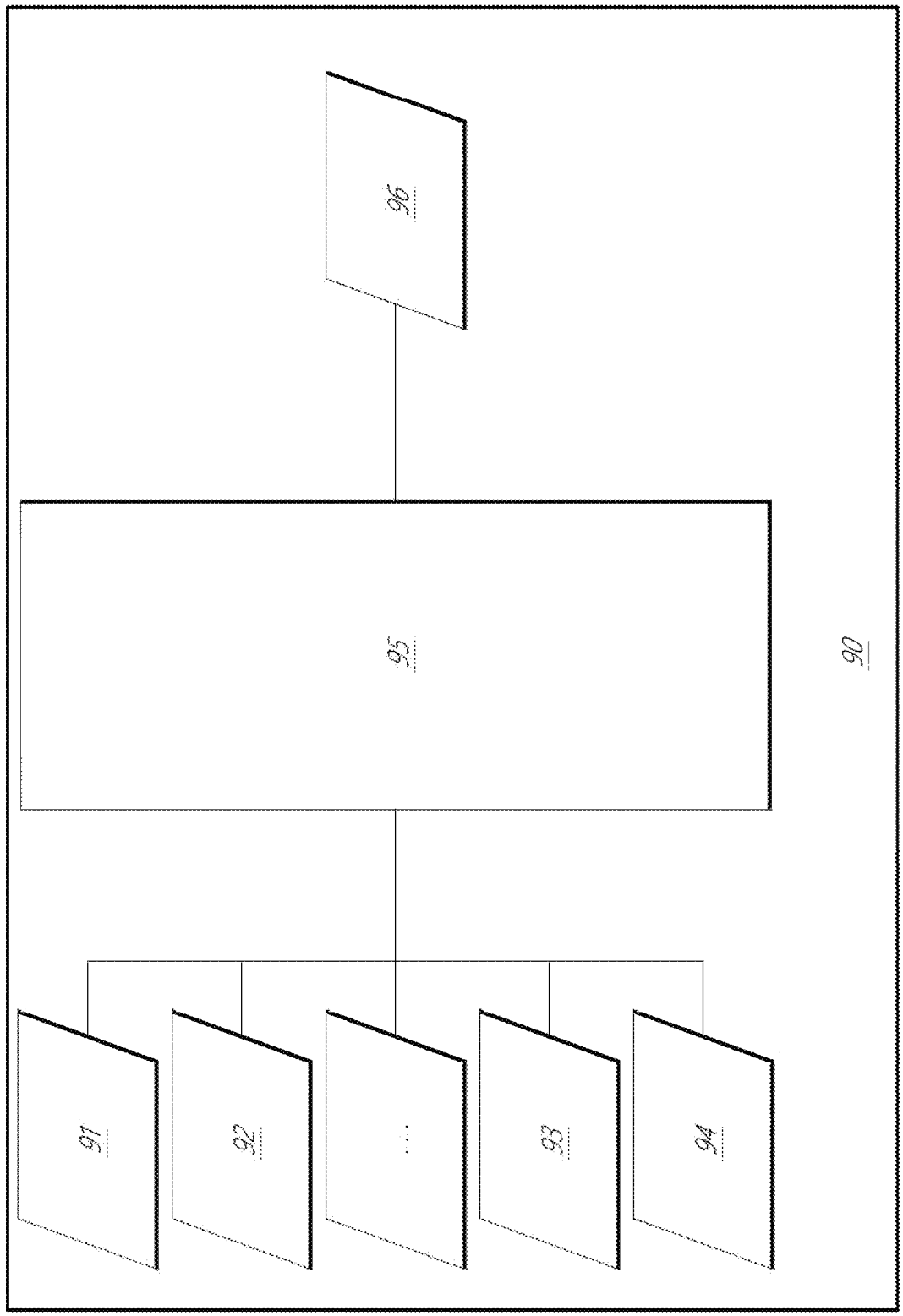
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Directed Fluidics

Embodiments of the disclosure relate to systems and techniques for removing an object from a treatment site of a patient, and in particular to methods and systems that employ directed fluidics during an object removal procedure.

During object removal procedures, fluidics (e.g., irrigation (inflow) and/or aspiration (outflow) of a liquid, such as saline) may be applied to the treatment site. During percutaneous nephrolithotomy (PCNL), for example, fluidics can be used to clear the visual field of stone dust and small fragments caused by the breakup of the kidney stone. As discussed in greater detail below, however, the conventional approach to fluidics during object removal procedures can also cause complications. For example, irrigation may create currents within the treatment site that move the object to be removed away from the medical instruments used during the procedure.

As used herein, the term "directed fluidics" applies to the methods, techniques, and systems described in this disclosure that improve on conventional fluidics, facilitate object removal procedures, and/or resolve or alleviate one or more problems associated with conventional object removal procedures. In general, directed fluidics involves controlling various features of the flow (e.g., rate, direction, pressure, position, etc.) of irrigation and/or aspiration and/or separating an inflow point (or points) of irrigation from an outflow point (or points) of aspiration to facilitate an object removal procedure. In some examples, directed fluidics involves providing irrigation and aspiration through a single medical instrument (e.g. a percutaneously inserted medical instrument), and may also involve controlling features of the irrigation and aspiration to facilitate object removal. In some examples, directed fluidics involves controlling a flow direction from an inflow point to an outflow point so as to, for example, hold or stabilize an object during the procedure. These and other features of directed fluidics, as well as various methods and systems for implementing directed fluidics during an object removal procedure, will become apparent from the following detailed description of several examples. The following examples are intended to illustrate the principles of this disclosure and should not be construed as limiting the disclosure.

In several of the examples described herein, the object removal procedure relates to removal of kidney stones from a kidney. This disclosure, however, is not limited only to kidney stone removal. For example, the following description is also applicable to other surgical or medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal.

A. Background Discussion of Object Removal.

As mentioned above, object removal is a common surgical operation or medical procedure. To better understand the features and advantages of the methods and systems for object removal that employ directed fluidics as described herein, this section first presents background information related to certain object removal procedures. By way of example, procedures for removing a kidney stone from a kidney are described.

Generally, there are several methods for treating patients with kidney stones, including observation, medical treatments (such as expulsion therapy), non-invasive treatments (such as extracorporeal shock wave lithotripsy (ESWL), and surgical treatments (such as ureteroscopy and PCNL). In the two surgical approaches (ureteroscopy and PCNL), the physician gains access to the pathology (i.e., the object to be removed; e.g., the stone), energy is delivered to the stone to break it into smaller pieces or fragments, and the small stone fragments/particulates are mechanically extracted from the kidney.

A component of PCNL is the use of fluidics (irrigation and aspiration). During PCNL, fluidics are applied to clear stone dust, small fragments, and thrombus from the treatment site as well as the visual field provided by the medical instruments.

Figure 16:
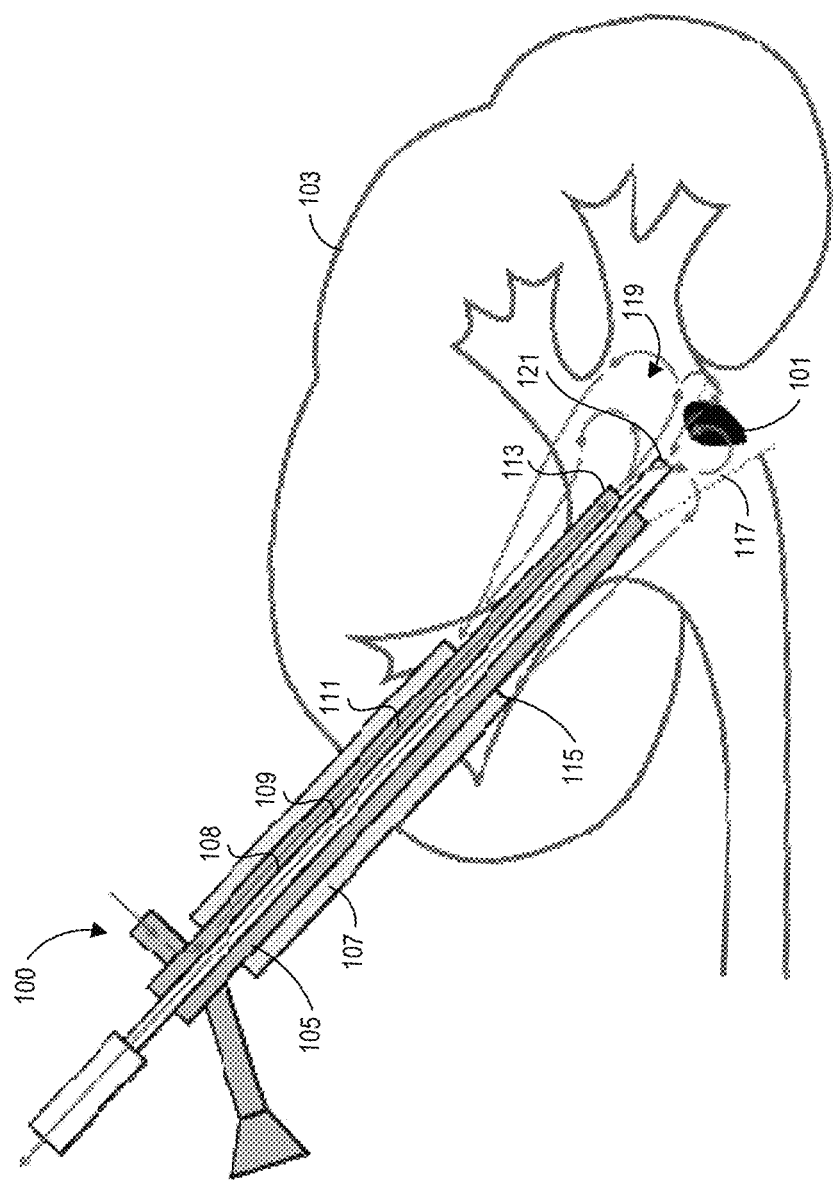
FIG. 16 illustrates an example procedure for removing an object from a kidney using a first medical instrument inserted into the kidney percutaneously.

FIG. 16 illustrates an example procedure for removing an object 101 from a kidney 103 using a medical instrument 100 inserted into the kidney 103 percutaneously. The illustrated example may be representative of a PCNL procedure. The object 101 can be any object that is targeted for removal, such as a kidney stone. In the illustrated example, the medical instrument 100 comprises a laparoscope or nephroscope 105. The nephroscope 105 can be inserted percutaneously into the kidney 103 through an access sheath 107. The nephroscope 105 can include a working channel 108, though which various tools can be inserted. As illustrated, a lithotripter 109 (such as an ultrasonic lithotripter) can be inserted through the working channel 108 of the nephroscope 105. The nephroscope 105 can also include an optic configured to allow a surgeon to visualize the treatment site. A field of view 117 of the optic is illustrated.

In general, the medical instrument 100 is navigated within the kidney 103 by torqueing the medical instrument 100 towards the object 101. The surgeon's goal is to touch the distal end 121 of the lithotripter 109 to the object 101 to break the object 101 into smaller fragments that can then be removed.

As illustrated with arrows in FIG. 16, irrigation (for example, of a saline solution) can be applied to the treatment site (e.g., the kidney 103) through the medical instrument 100. In this example, irrigation passes through the nephroscope 105, exiting through a distal tip 113 into the kidney 103. Irrigation can be used to clear stone dust and small fragments from the field of view 117 to allow the surgeon to visualize the treatment site, as well as to distend the kidney 103 to allow access to the object 101. In the illustrated example, aspiration is also applied to the treatment site through the medical instrument 100. As shown, liquid can be removed from the kidney 103 through the access sheath 107 as well as through a channel in the lithotripter 109. In some instances, irrigation is pumped (actively) through the lithotripter 109, while the remainder of the irrigation through the access sheath 107 is passive (e.g., passively flowing through the access sheath 107). In some examples, fluidics are applied during the entire procedure.

The fluidics applied during the procedure can establish a fluid flow as illustrated by the arrows in FIG. 16. Initially, fluid can flow outward from the distal tip 113 of the nephroscope 105 towards the object 101. Irrigation through the access sheath 107 and lithotripter 109 can cause fluid flow back towards the medical instrument 100. As illustrated, in the region of the object 101, the flow is both directed toward and away from the object 101 with respect to the distal end of the medical instrument 100. In some instances, the net effect of such a flow may be that many small and unpredictable eddies 119 are formed around the object 101 and the distal end of the medical instrument 100. This may result in the object 101 being pushed away from the medical instrument 100. This can prevent the surgeon from contacting the lithotripter 109 to the object 101 and/or scatter the fragments created by the lithotripter 109 as the stone is broken up. These difficulties may arise when only irrigation is actively managed, while aspiration is passive, thus not allowing for a high degree of fluidic control during the procedure. Another potential danger is that the kidney 103 may become overfilled.

As another example, during a ureteroscopic lithotripsy, a ureteroscope may enter the kidney through the ureter and use stone-retrieval baskets and lithotripters to relocate and break down kidney stones, respectively. For example, a lithotripter can be deployed through the ureteroscope and used to break the stone into fragments. During the lithotripsy of the kidney stones, several problems can occur. For example, the lithotripter (which applies energy to break up the stone) can cause the stone to move around unpredictably within the kidney. Further, as described above, lithotripsy generates stone dust, which can obstruct vision within the treatment site. After the stone has been broken down, the lithotripter can be removed and a basketing device can be deployed through the ureteroscope to retrieve the stone fragments. This process can be both tedious and time consuming. After attempting to remove all stone fragments by basketing, there may be small stone debris that remain.

The procedures for kidney stone removal discussed above (PCNL and ureteroscopy) may exhibit certain challenges or complications. For example, PCNL may use fluidics that create currents within the kidney that can move the object and fragments away from medical instrument, complicating the removal process. Ureteroscopy may use a lithotripter employed through a ureteroscope to break up the kidney stone; however, there may be no mechanism in place to stabilize the stone during lithotripsy. Often, the energy used to break up the stone causes the stone to bounce away from the lithotripter, complicating removal. Further, as the stone is broken down via lithotripsy, stone dust is generated which obstructs vision of the treatment site. Another challenge with these procedures is that it may be difficult for the physician to gain access to the treatment site because of the surrounding anatomy outside of the kidney. For example, locations for percutaneous access to the kidney may be limited due to the surrounding anatomy outside of the kidney.

B. Overview of Object Removal with Directed Fluidics.

The methods and systems described herein may be used to alleviate or resolve one or more of the problems of PCNL and ureteroscopy (described above) through the use of directed fluidics. In some embodiments, directed fluidics can be applied such that irrigation (inflow) enters the treatment site through a first channel of a first medical device (e.g., a percutaneously inserted medical instrument) and aspiration (outflow) exits the treatment site through a second channel of the first medical instrument. In some embodiments, irrigation and aspiration can both be active. In some embodiments, irrigation and aspiration can be managed to produce desirable flow characteristics. In some embodiments, a second medical instrument that does not provide irrigation or aspiration can also be used during the procedure, for example, to break up the object being removed. In some embodiments, directed fluidics can be applied such that irrigation (inflow) enters the treatment site through a first medical device (e.g., a catheter or endoscope), while aspiration (outflow) exits the treatment site through a second medical instrument (e.g., a catheter or endoscope). This can create a controlled flow from the first instrument towards the second instrument. The controlled flow can facilitate object removal. The first medical instrument can be inserted into the treatment site antegrade of the object to be removed, while the second medical instrument can be inserted into the treatment site retrograde of the object. The first medical instrument can be inserted through a patient lumen or percutaneously. The second medical instrument can be inserted through a patient lumen or percutaneously. In some embodiments, the first medical instrument is inserted into the treatment site (e.g., the kidney) through a patient lumen (e.g., the ureter) and the second medical instrument is inserted into the treatment site percutaneously, or vice versa.

One or both of the first and second medical instruments can be robotically controlled medical instruments as described above with reference to FIGS. 1-15. Accordingly, the methods and systems described below can be employed robotically in some embodiments.

In some instances, directed fluidics can include the separation of the point(s) of inflow (irrigation) from the point(s) of outflow (aspiration). The inflow can be directed towards the point of outflow, for example by deflecting the distal end of a first medical instrument towards a second medical instrument such that the fluid flow is towards the second medical instrument. This may be accomplished robotically and/or automatically with the systems and instruments described above with reference to FIGS. 1-15. In some embodiments, the point of inflow (irrigation) does not need to be directional (i.e., pointed in a specific direction), provided that the first medical instrument is configured to achieve a sufficiently high inflow rate without causing turbulence. This may allow the treatment site (e.g., the kidney) to fill up with fluid without displacing the stone. In some embodiments, the point of outflow (aspiration) may be a single or concentrated point. The point of outflow may be configured to provide high flow with high velocities so as to cause fragments to be pulled towards the point of outflow.

In some embodiments, the irrigation and aspiration rates can be modulated to improve stone displacement or stabilization or to intentionally create turbulence so that the irrigation reaches all corners of the treatment site. For example, a gentle alternating cycle of irrigation and aspiration can create a lavage like effect to preferentially pull large stone debris away from calyces and towards the aspiration site. Alternatively, short pulsatile inflow and outflow could be used to create turbulence and ensure that smaller and lighter stone fragments do not settle on the floor of the treatment site, but instead remain floating in the irrigant and eventually get aspirated with the outflow.

Figure 17:
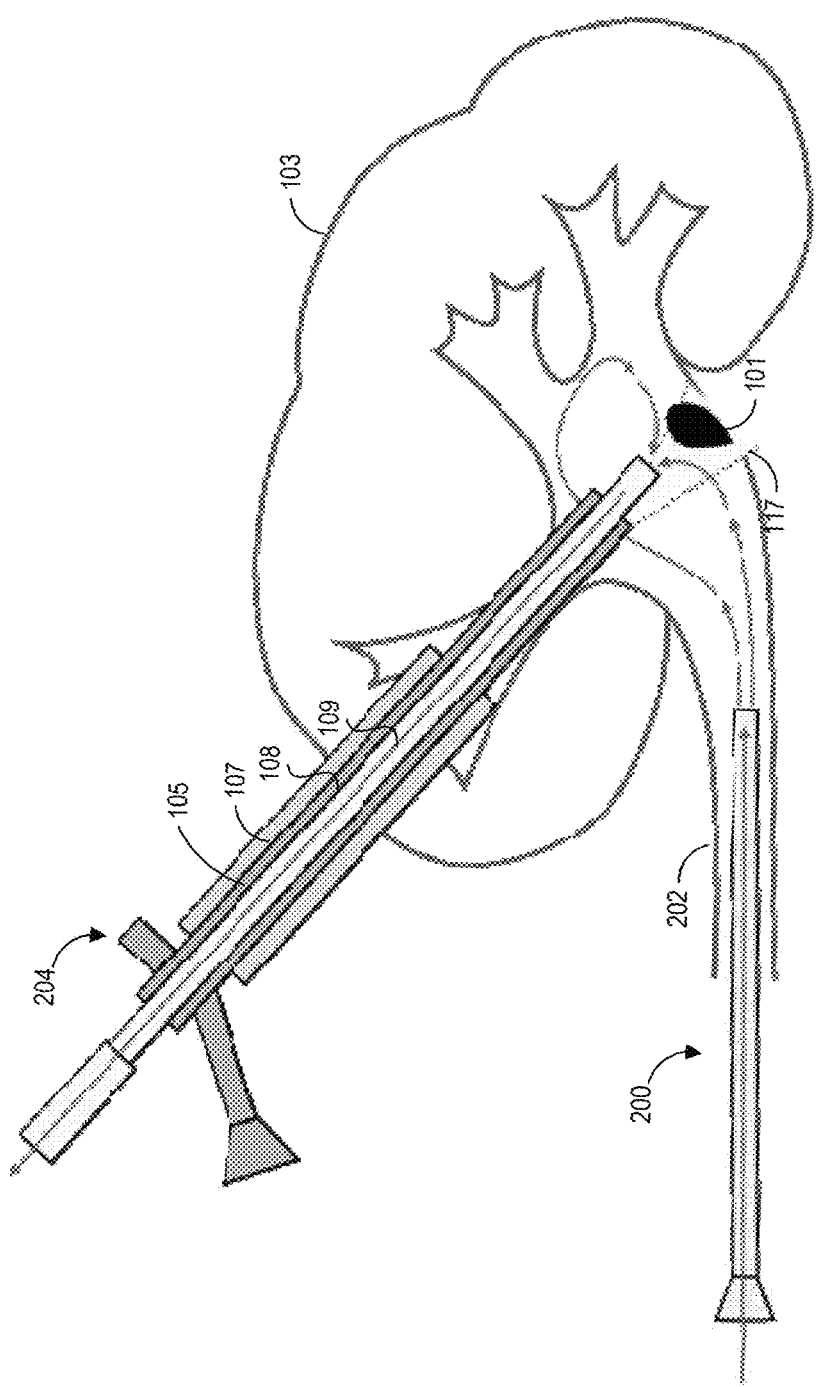
FIG. 17 illustrates an example procedure for removing an object from a kidney using a first medical instrument inserted into the kidney through a patient lumen, a second medical instrument inserted into the kidney percutaneously, and directed fluidics.

FIG. 17 illustrates an example procedure for removing an object 101 from a kidney 103 using a first medical instrument 200 inserted into the kidney 103 through a patient lumen 202, a second medical instrument 204 inserted into the kidney percutaneously, and directed fluidics. In the illustrated example of FIG. 17, the first medical instrument 200 comprises an endoscope, such as a ureteroscope. The patient lumen 202 can comprise the ureter. The first medical instrument 200 can include a channel for supplying irrigation. The channel can be connected to an irrigation source and a pump (see FIG. 25). The first medical instrument 200 may be articulable. The first medical instrument 200 may be robotically controlled.

As illustrated, the second medical instrument 204 can include a nephroscope 105. The nephroscope 105 can be a rigid nephroscope. The nephroscope 105 can be inserted percutaneously into the kidney 103 through an access sheath 107. The nephroscope 105 can include a working channel 108, though which various tools can be inserted or that may be used as channels for aspiration or irrigation. In some embodiments, other channels within the nephroscope can be used for aspiration and irrigation. As illustrated, a lithotripter 109 (such as an ultrasonic lithotripter) may be inserted through the working channel 108 of the nephroscope 105. The nephroscope 105 can also include an optic configured to allow a surgeon to visualize the treatment site. A field of view 117 of the optic is illustrated.

Fluid flow is illustrated with arrows in FIG. 17. As shown, irrigation is provided through the first medical instrument 200 and aspiration is provided through the second medical instrument 204. In the illustrated embodiment, irrigation is provided through the lithotripter 109, but irrigation could be provided alternatively (or additionally) through the nephroscope 105 and/or access sheath 107. As shown, the points of inflow (irrigation) and outflow (aspiration) are separated and a general flow direction is established from the first medical instrument 200 to the second medical instrument 204.

As mentioned above, the second medical instrument 204 may include an optic (e.g., a camera) for visualizing the treatment site (with field of view 117). Because flow is directed continuously away from the first instrument 200 and towards the second instrument 204, the field of view 117 of the optic can remain clear, allowing improved visualization of the treatment site. Further, because flow is directed towards the second medical instrument 204, which includes the lithotripter 109, the object 101 and fragments can be pushed towards the second medical instrument 204, beneficially facilitating contact with the lithotripter 109.

This concept of directed fluidics allows debris, dust, thrombus, and fragments to naturally flow towards the second medical instrument 204 and into the stone extraction or destruction device (lithotripter 109). In the event that the physician is required to pursue fragments, he or she may need to maneuver the devices to a lesser extent than during other procedures owed to the tendency of fragments to flow toward rather than away from the second medical device 204.

Additionally, in the event that irrigation is provided through the nephroscope 105 and/or access sheath 107, this may enable the use of a much larger diameter lithotripter 109 because the irrigation and/or aspiration no longer need to be provided through the lithotripter 109.

In another example, the second instrument 204 can be an articulable catheter that is introduced via percutaneous access into the treatment site (e.g., the kidney) (see FIGS. 18, 19, 26A, and 26B). The catheter can be configured to be able to navigate within the kidney. For example, the catheter may be configured to be inserted and retracted into the treatment site and/or to articulate (e.g., bend). In some embodiments, the catheter can include pull-wires for controlling articulation. In some embodiments, four pull-wires are oriented in the four orthogonal directions to enable articulation of the catheter. Other methods for permitting articulation of the catheter are also possible. The catheter can include, for example, an aspiration lumen (or channel). The aspiration lumen can be connected to a pump. The pump may be an external pump. The pump may generate negative pressure that causes flow from the treatment site into the catheter. The aspiration function may be able to be toggled (e.g., on and off) and adjusted by the user or system. In some embodiments, the aspiration lumen may be used for irrigation.

The catheter can provide several functions during an object removal procedure employing directed fluidics. For example, the catheter can stabilize the stone during lithotripsy. If the stone is larger than the aspiration lumen of the catheter, the stone can be held at the distal face of the aspiration lumen, thus stabilizing the stone while it is broken down to dust and smaller fragments. The aspiration flow may hold the stone to the distal face. This may provide the user with a less mobile target for lithotripsy.

The catheter can improve visibility of the treatment site. The catheter can remove stone dust from the kidney. This can provide the user with improved visibility (e.g., continuously adequate visibility), for example, from an imaging device inserted into the treatment site (for example, on a medical instrument inserted into the treatment site).

The catheter can remove stone dust and fragments. The fluid flow can carry fluid and debris into the catheter. The debris may be cleared as it is generated (i.e., while the stone is being broken up). The removal of debris via the catheter can take the place of removal of fragments via ureteroscopic basketing, which can be time consuming due to the difficulty of closing the basket around the stone, and due to the need to remove and re-insert the ureteroscope during each fragment removal. This can result in a more efficient removal procedure. Such a procedure may be completed faster because, for example, fragments are removed as the stone is broken up. Removing stone debris via the catheter can also reduce the risk of the stone fragment injuring tissue (such as during removal of stone through the ureter).

The catheter can be used to relocate kidney stones. For example, the catheter can be configured to navigate within the kidney towards stone or stone debris. With aspiration, the stone or stone debris can be held onto the distal tip of the catheter, and moved to another location within the kidney. This function may remove or reduce the need to use a basket device to relocate or move the stone. The catheter can also be configured to be advanced into the ureter to retrieve stones or fragments that have migrated into the ureter. This may allow a physician to perform the procedure without ureteral protection devices that are sometimes employed during certain procedures.

The catheter can be used in several ways during a procedure. For example, the catheter can be mobile throughout the procedure. The catheter can navigate around the treatment site to target specific stones/fragments in order to constrain them during lithotripsy, while also aspirating dust/debris. As another example, the catheter can be initially stationary during the procedure and the first medical instrument (e.g., a ureteroscope) could be used to relocate stones to the catheter. The stones could be broken down at the catheter. At a later time during the procedure, the catheter could navigate through the treatment site to pick up remaining debris. As another example, the catheter could be inserted (e.g., percutaneously) only when required, for example, during procedure escalation.

Figure 18:
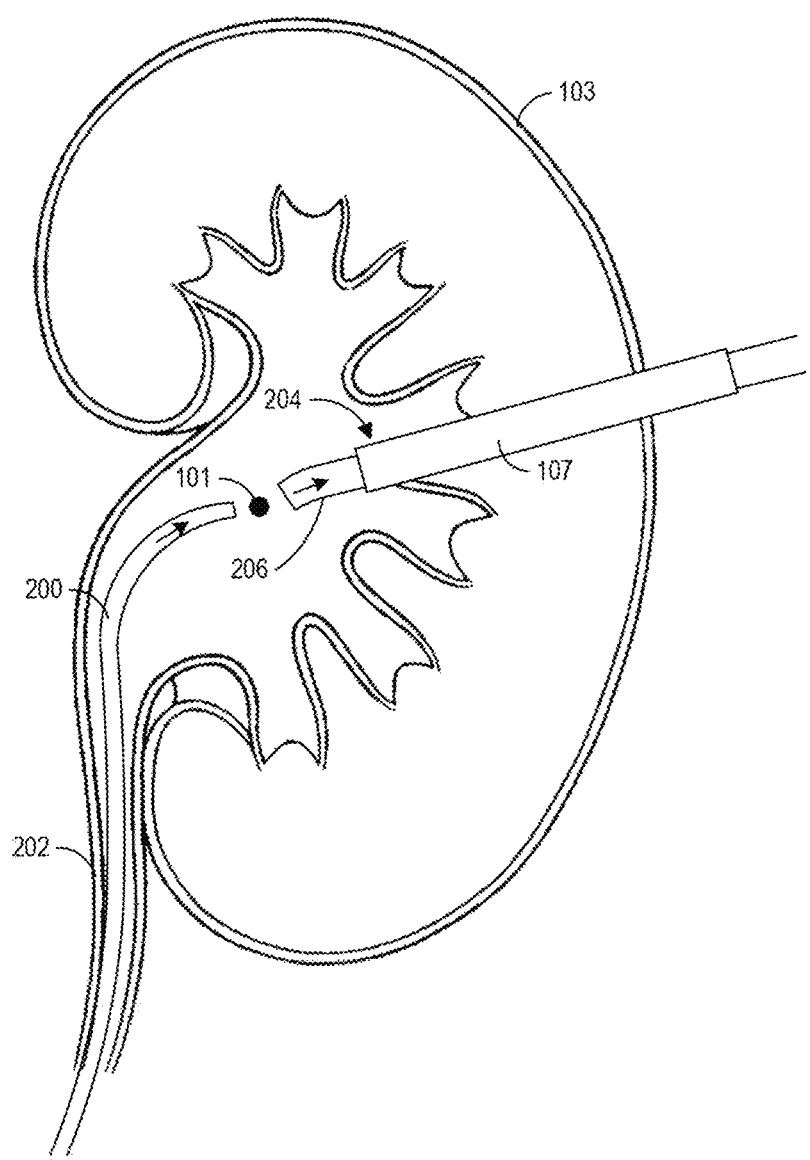
FIG. 18 illustrates another example procedure for removing an object from a kidney using a first medical instrument inserted into the kidney through a patient lumen, a second medical instrument inserted into the kidney percutaneously, and directed fluidics.

FIG. 18 illustrates an example procedure for removing an object 101 from a kidney 103 using a first medical instrument 200 inserted into the kidney 103 through a patient lumen 202, a second medical instrument 204, such as a steerable catheter, inserted into the kidney 103 percutaneously (for example, through an access sheath 107), and directed fluidics. Irrigation may be provided through the first medical instrument 200 and aspiration may be provided through the second medical instrument 204. In this example, the points of inflow (irrigation) and outflow (aspiration) are separated and a general flow direction is established from the first medical instrument 200 towards the second medical instrument 204. Arrows illustrate the direction of fluid flow.

As illustrated in FIG. 18, the first medical instrument 200 can be articulable. That is the shape or pose of the first medical instrument 200 can be controlled. In some embodiments, the articulation is controlled robotically as described above. As illustrated, the first medical instrument 200 can be articulated such that the irrigation flow is oriented or directed towards the second medical instrument 204. This may help establish the fluid flow from the first medical instrument 200 towards the second medical instrument 204.

The second medical instrument 204 (e.g., the steerable catheter) can also be articulable. That is the shape or pose of the second medical instrument 204 can be controlled. In some embodiments, the articulation is controlled robotically as described above. As illustrated, the second medical instrument 204 can include an articulable distal tip 206. The second medical instrument 204 (or the distal tip 206 thereof) can be articulated such that that the distal tip 206 is oriented or directed towards the first medical instrument 200 and/or the object 101. This may help establish the fluid flow from the first medical instrument 200 towards the second medical instrument 204, thereby serving to pull the object 101 towards the second medical instrument 204.

Figure 19:
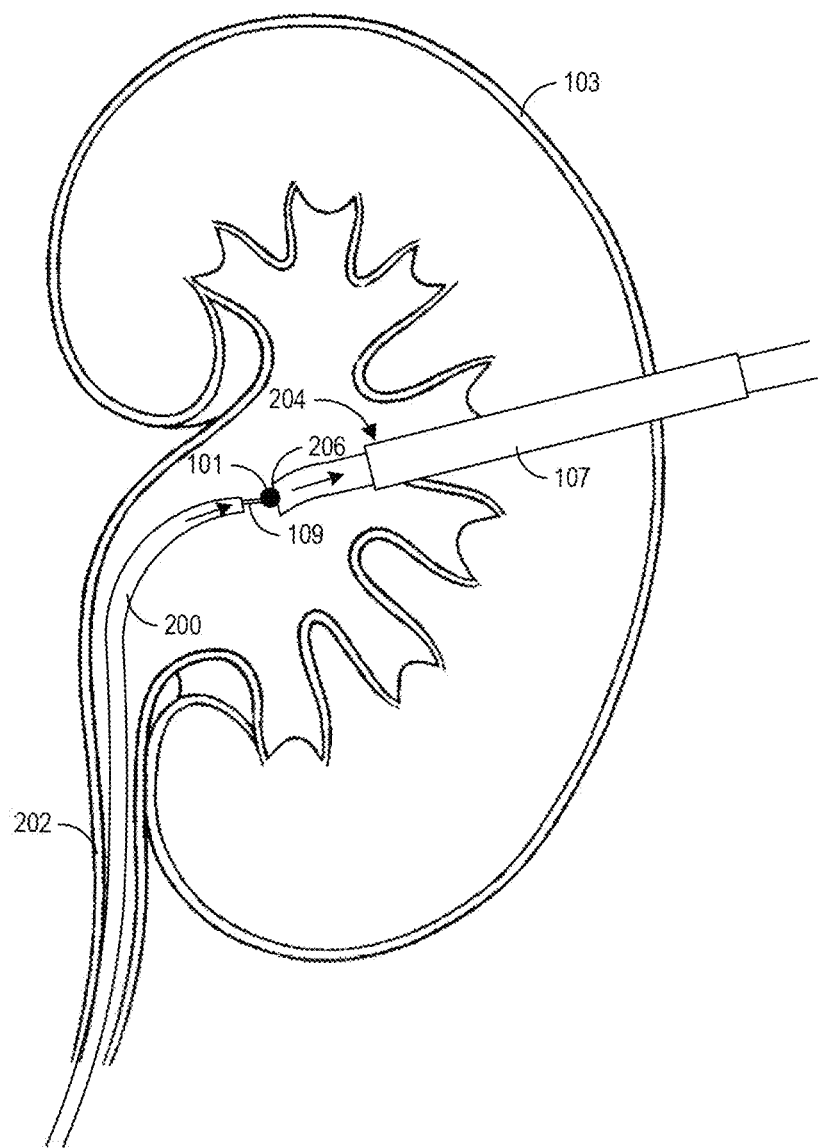
FIG. 19 illustrates another example procedure for removing an object from a kidney using a first medical instrument inserted into the kidney through a patient lumen, a second medical instrument inserted into the kidney percutaneously, and directed fluidics.

FIG. 19 illustrates another example procedure for removing an object 101 from a kidney 103 using a first medical instrument 200 inserted into the kidney 103 through a patient lumen 202, a second medical instrument 204 (such as a steerable catheter) inserted into the kidney 103 percutaneously (for example, through an access sheath 107), and directed fluidics. In the illustrated example, the first medical instrument 200 includes a lithotripter 109. Fluid flow from the first medical instrument 200 to the second medical instrument 204 can be used to hold the object 101 and/or fragments onto the distal tip 206 of the second medical instrument 204. This can stabilize the object 101 and/or fragments during lithotripsy with the lithotripter 109 of first medical instrument 200. The distal tip 206 of the second medical instrument 204 can include a pocket (or other holding device) on its distal tip to stabilize and hold the object 101 and/or fragments. See, for example, FIGS. 26A and 26B described below.

Figure 20:
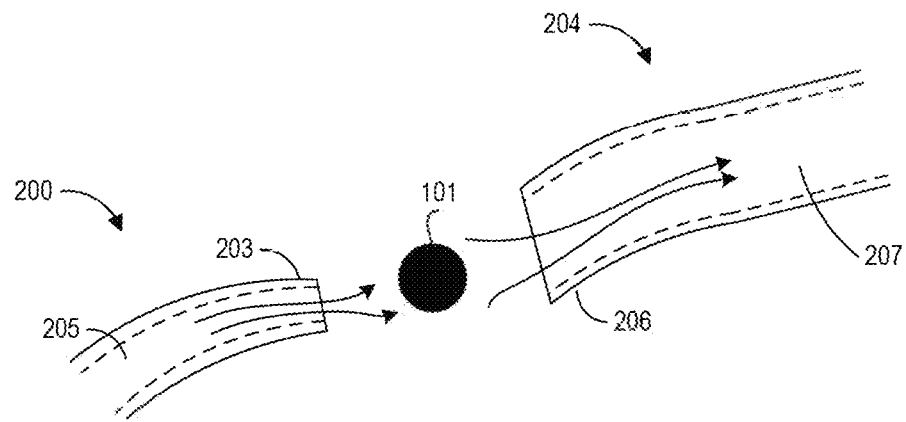
FIG. 20 illustrates a detailed view of a distal tip of a first medical instrument providing irrigation and a distal tip of a second medical instrument providing aspiration during an object removal procedure.

FIG. 20 provides a detailed view of a distal tip 203 of the first medical instrument 200 (providing irrigation) and a distal tip 206 of the second medical 204 instrument (providing aspiration during) an object removal procedure. Arrows illustrate the direction of flow from the first medical instrument 200 to the second medical instrument 204. As shown, irrigation passes through a first fluid channel 205 in the first medical instrument 200 and exits at a distal tip 203. Aspiration is provided through the distal tip 206 and second fluid channel 207. As shown, the flow directs the object 101 towards the distal tip 206 of the second medical instrument 204.

In some examples, the catheter can also have the ability to provide irrigation of fluid into the kidney (in addition to the aspiration described above). For example, an irrigation channel of the catheter can start at the proximal end of the catheter and can include the annular space between the catheter shaft and the aspiration lumen tubing. The distal end of the catheter can include irrigation openings. For example, the catheter can include circumferential holes (e.g. four holes) from which the irrigation fluid exits. The irrigation may be toggled on/off by the user or system. The irrigation may be connected to a fluidics system that has the ability to balance or otherwise modify the irrigation/aspiration levels as described herein.

Figure 21A:
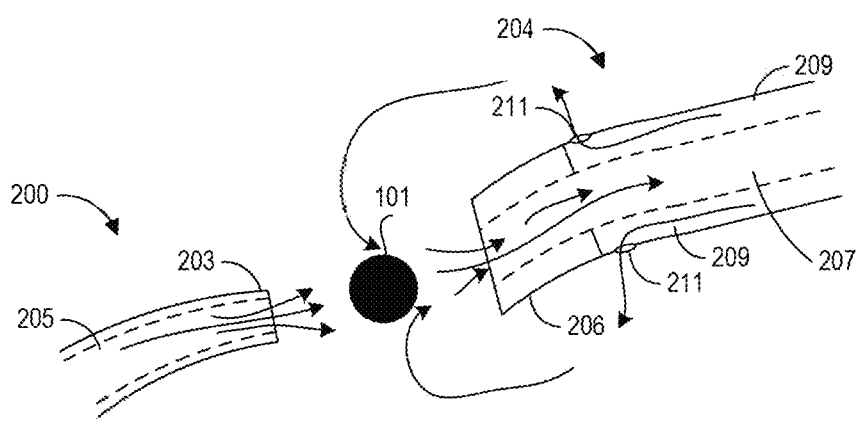
FIG. 21A illustrates a detailed view of a distal tip of a first medical instrument providing irrigation and a distal tip of a second medical instrument providing irrigation and aspiration during an object removal procedure.

FIG. 21A provides a detailed view of a distal tip of a first medical instrument 200 providing irrigation and a distal tip 206 of a second medical instrument 204 providing both irrigation and aspiration during an object removal procedure (see also FIGS. 26A and 26B described below). Arrows illustrate the direction of flow from the first medical instrument 200 to the second medical instrument 204. As shown, in this example, irrigation passes through a first fluid channel 205 in the first medical instrument 200 and exits at a distal tip 203. Similar to FIG. 20, aspiration is provided through the distal tip 206 and second fluid channel 207 of the second medical instrument 204. However, the second medical instrument 204 also includes additional fluid channels 209 for supplying irrigation. The additional fluid channels 209 can annularly surround the second fluid channel 207. In the illustrated embodiments, the additional fluid channels 209 terminate at fluid outlets 211 near the distal tip 206 of the second medical instrument 204. In some embodiments, the fluid outlets 211 can direct the irrigation from the second medical instrument 204 away from the distal tip 206. In some embodiments, the fluid outlets 211 can direct the irrigation radially away from the distal tip 206. As shown, the flow can direct the object 101 towards the distal tip 206 of the second medical instrument 204.

Figure 21B:
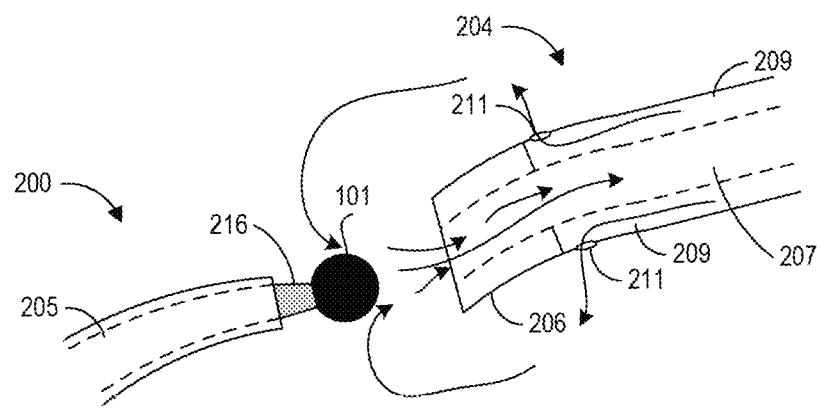
FIG. 21B illustrates a detailed view of a distal tip of a first medical instrument performing lithotomy and a distal tip of a second medical instrument providing irrigation and aspiration during an object removal procedure.

In some implementations, irrigation and aspiration can be provided through a single medical instrument, while another medical instrument may be used for performing additional aspects of the procedure. For example, FIG. 21B provides a detailed view of a distal tip of a first medical instrument 200 performing lithotomy with a lithotripter 216 and a distal tip 206 of a second medical instrument 204 providing both irrigation and aspiration during an object removal procedure. The second medical instrument 204 may be similar to the instrument 700 described below with reference to FIGS.

26A and 26B. As shown, in this example, only the second instrument 204 is used to provide fluidics. Both irrigation and aspiration are provided through the second instrument 204.

Directed fluidics can provide one or more of the following advantages. During a ureteroscopic lithotripsy, the kidney stone can move around and migrate within the kidney. The energy from the lithotripter may exacerbate this movement. Directed fluidics, with or without a catheter that provides both aspiration and irrigation, can use aspiration to constrain these unwanted stone movements. For example, the fluid flow can hold the stone to the distal end of the instrument.

Additionally, during lithotripsy, small dust particles form, which can obscure vision through the ureteroscope. In some ureteroscopic lithotripsy, the vision can become so obscured that the procedure must be stopped. Directed fluidics, with or without a catheter that provides both aspiration and irrigation, can provide the advantage of aspirating the dust particles (or other matter) out of the treatment site, providing the user with continuous good visibility.

Additionally, basketing can be time consuming due to the difficulty of capturing stone fragments within a basket and then removing the entire ureteroscope from the patient for each fragment removal. Directed fluidics can provide the advantage of quick removal of stone fragments as they are formed.

Finally, during some ureteroscopic lithotripsy, if a kidney stone needs to be relocated, a basket retrieval device is often used, which may be time consuming due to the need to position the stone in the basket, and due to the need to exchange the lithotripter for the basket retrieval device. Directed fluidics can provide the advantage of navigating the catheter through the kidney and using aspiration to hold onto the stone, and then relocating the stone to another location in the kidney by moving the aspiration catheter.

C. Example Methods for Directed Fluidics.

Figure 22A:
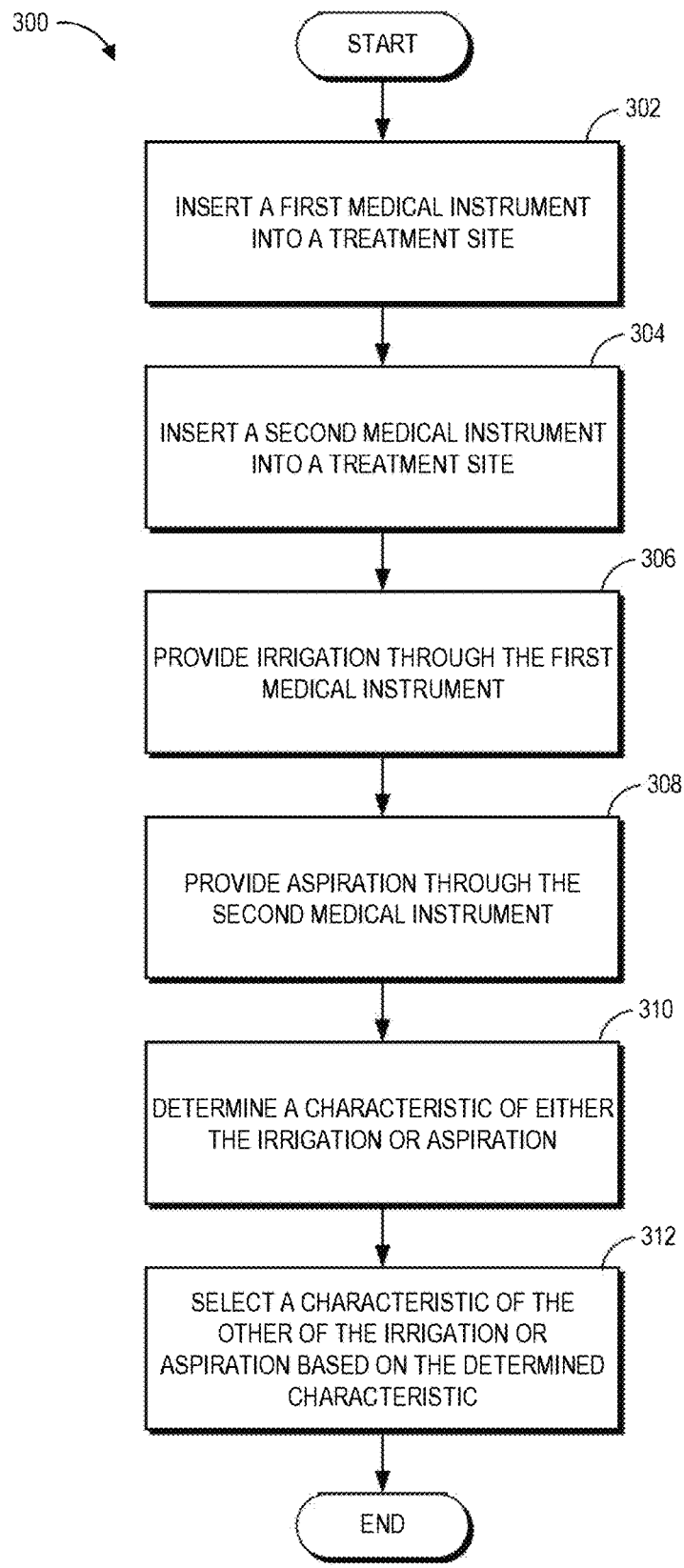
FIG. 22A is a flowchart illustrating an embodiment of a method for directed fluidics during an object removal procedure.

FIG. 22A is a flowchart illustrating an embodiment of a method 300 for administering directed fluidics during a medical procedure, such as an object removal procedure. In some examples, the object removal procedure is a procedure for removing a kidney stone from a kidney. The method 300 can be also be implemented in other types of medical procedures and in other treatment sites. In some embodiments, the method 300 is implemented in a robotic medical system, for example, any of the systems described above with reference to FIGS. 1-15.

The method 300 begins at block 302. At block 302, a first medical instrument is inserted into a treatment site. The first medical instrument can be inserted through a lumen of the patient. In the example of kidney stone removal, the patient lumen may be the ureter. In some examples, the first medical instrument can be inserted percutaneously into the treatment site. The first medical instrument can be an endoscope, nephroscope, catheter, or other type of medical instrument. The first medical instrument can be articulable. In some examples, the first medical instrument is not articulable. In some embodiments, the first medical instrument can include one or more working channels configured to receive various tools (e.g., lithotripters, basket retrieval devices, forceps, etc.) therethrough. The first medical instrument can include at least one first fluid channel. The first fluid channel can be configured to provide fluidics to the treatment site during the medical procedure.

At block 304, a second medical instrument is inserted into the treatment site. The second medical instrument can be inserted through a lumen of the patient. In the example of kidney stone removal, the patient lumen may be the ureter. In some examples, the second medical instrument can be inserted percutaneously into the treatment site. The second medical instrument can be an endoscope, nephroscope, catheter, or other type of medical instrument. The second medical instrument can be articulable. In some examples, the second medical instrument is not articulable. The second medical instrument can include one or more working channels configured to receive various tools (e.g., lithotripters, basket retrieval devices, forceps, etc.) therethrough. The second medical instrument can include at least one second fluid channel. The second fluid channel can be configured to provide fluidics to the treatment site during the medical procedure.

In some instances, the order of block 302 and block 304 can be reversed. In some instances, block 302 and block 304 can be performed at the same time.

In some instances, the first and second medical devices are inserted into the treatment site via different methods of access. For example, the first medical instrument may be inserted through a patient lumen and the second medical instrument may be inserted percutaneously, or vice versa. As another example, the first medical instrument can be inserted into the treatment site through a first patient lumen, and the second medical instrument can be inserted into the treatment side through a second patient lumen different than the first patient lumen. As another example, the first medical device can be inserted through a first percutaneous access, and the second medical device can be inserted through a second percutaneous access different than the first percutaneous access. In some examples, the first and second medical devices are inserted through the same patient lumen or through the same percutaneous access.

In some instances, the first and second medical devices are inserted into the treatment site such that the distal ends of the first and second medical devices are separated within the treatment site. For example, the distal end of the first medical device can be positioned antegrade of the object to be removed, and the distal end of the second medical device can be positioned retrograde of the object to be removed. As another example, the distal end of the medical device can be positioned retrograde of the object to be removed, and the distal end of the second medical device can be positioned antegrade of the object to be removed. In some instances, the first and second medical devices are positioned such that the object is positioned between the distal ends of the first and second medical devices.

In some instances, the distal end of the first medical device can be oriented (e.g., directed or pointed) towards the distal end of the second medical device. Alternatively or additionally, the distal end of the second medical device can be oriented towards the distal end of first medical device. In some examples, "pointing towards" can refer to a general axis or direction of fluid flow entering or exiting the first or second fluid channel of the first or second medical instrument. In some embodiments, the distal ends of the first and second medical devices can include position sensors. The position sensors can be EM sensors. The EM sensors can be configured to provide position information regarding the distal ends of the first and second medical devices and/or orientation information regarding the distal ends of the first and second medical devices. Other types of position and orientation sensors can be used. An output of the position sensors may be used to orient that first and second medical instruments. In some embodiments, the first and second medical instruments can be oriented visually or through other methods.

In some instances, the distal end of the first medical instrument can be brought into contact with the object to be removed. Alternatively or additionally, the distal end of the second medical instrument can be brought into contact with the object to be removed. In some embodiments, neither instrument contacts the object to be removed.

At block 306, irrigation is provided through the first medical instrument. For example, irrigation can be provided through the first fluid channel of the first medical instrument. The first fluid channel can be connected to an irrigation source through a pump. The irrigation source can provide a fluid irrigant (such as saline) for irrigating the treatment site. The pump can be configured to move the irrigant through the fluid channel and into the treatment site. In one example, the pump is a peristaltic pump. The pump can be configured to set a specific flowrate through the first medical instrument. In another example, the pump can be a vacuum source configured to apply a negative pressure that draws the irrigant from the irrigation source, out through the first medical instrument, and into the treatment site. Flow rate can be varied by adjusting the vacuum pressure.

At block 308, aspiration is provided through the second medical instrument. For example, aspiration can be provided through the second fluid channel of the second medical instrument. The second fluid channel can be connected to a collection container through a vacuum. The vacuum can be configured to apply a negative pressure that draws the fluid (e.g., the irrigant) from the treatment site, through the second medical instrument, and into the collection container. Flow rate can be varied by adjusting the vacuum pressure. In another example, the vacuum can be replaced with a pump, such as peristaltic pump. The pump can be used to move fluid (e.g., the irrigant) from the treatment site, through the second medical instrument, and into the collection container. The pump or vacuum can be configured to set a specific flowrate through the second medical instrument.

In some instances, the order of blocks 306 and block 308 can be reversed. In some instances, block 306 and block 308 can be performed at the same time. In some instances, block 306 and block 308 can be performed alternatingly, such that irrigation is provided, followed by aspiration, in a series of repetitive steps, for example.

At block 310, the method 300 determines a characteristic of either the irrigation or the aspiration. The characteristic can be an instantaneous flow rate of the irrigation or aspiration. The characteristic can be an average flow rate of the irrigation or aspiration over a time interval. The time interval can be, for example, 1.0 seconds, 2.5, second, 5 second, 10 second, 15 seconds or longer, as well as intervals above and below the listed values. The characteristic can be a volume of fluid irrigated or aspirated during a time interval, such as, for example, any of the time intervals listed above. The characteristic can be an instantaneous fluid pressure associated with the irrigation or aspiration. The characteristic can be an average fluid pressure associated with the irrigation or aspiration over a time interval, such as, for example, any of the time intervals listed above. The fluid pressure can be, for example, a fluid pressure within the first fluid channel, a fluid pressure within the second fluid channel, or a fluid pressure within the treatment site itself.

In some instances, the characteristic is determined using one or more sensors. The sensor can be positioned, for example, in the first fluid channel, on the first medical instrument, in the second fluid channel, on the second medical instrument, or otherwise within in the treatment site. The sensor can be a flow rate sensor, a pressure sensor, or other sensor for determining a characteristic of the irrigation or aspiration. In some embodiments, the sensor can measure intrarenal pressure. In some instances, the characteristic is determined from the pump or vacuum source supplying the irrigation or aspiration. For example, the characteristic can be determined based on a flow rate set by the pump or a vacuum pressure applied by the vacuum source. In some instances, the characteristic is calculated from one or more known or measured parameters. For example, the characteristic can comprise a volume of irrigant within the treatment site calculated based on the amount of irrigant pumped into the treatment site.

At block 312, the method 300 selects (e.g., sets or adjusts) a characteristic of the other of the irrigation or aspiration based on the characteristic of the irrigation or aspiration determined at block 310. For example, if a characteristic of aspiration of is determined at block 310, a characteristic of irrigation is selected at block 312 based on the determined characteristic. If a characteristic of irrigation of is determined at block 310, a characteristic of aspiration is selected at block 312 based on the determined characteristic.

The selected characteristic may be any of the characteristics described above with reference to the determined characteristic of block 310. For example, the selected characteristic can be instantaneous or average flow rate, fluid volume, pressure, etc.

In some instances, the selected characteristic may correspond with the determined characteristic. For example, if instantaneous flow rate of the irrigation is determined, flow rate of the aspiration is selected. This need not be the case in all instances. For example, a volume of irrigation can be determined and an instantaneous flow rate or pressure associated with aspiration can be adjusted. In some instances, the selected characteristic is selected to match the determined characteristic. For example, if a flow rate of x mL/sec of irrigation is determined, the flow rate of aspiration can be selected to match that is the flow rate of aspiration can be selected to be x mL/sec, such that the flow rates of irrigation and aspiration match. This need not be the case in all embodiments. For example, if a flow rate of x mL/sec of irrigation is determined, the flow rate of aspiration can be selected based on the determined flow rate, without exactly matching—that is the flow rate of aspiration can be selected to be y mL/sec, such that the flow rates of irrigation and aspiration do not exactly match. In some embodiments, the determined and selected characteristics are related but do not exactly match. For example, the flow rate of aspiration can be greater than, less than, or equal to the flow rate of irrigation.

With blocks 310 and 312, one of aspiration and irrigation can be adjusted based on the other of aspiration or irrigation. The method 300 thus provides a way for balancing (e.g., instantaneously or over a period of time) aspiration and irrigation. The method 300 also provides a mechanism for regulating a condition of the treatment site. For example, by balancing irrigation and aspiration, an internal fluid volume or pressure of the treatment site can be adjusted or maintained. The method 300 also provides a mechanism for regulating a condition of the fluid flow. For example, by balancing irrigation and aspiration, flow rate between the first medical instrument and the second medical instrument can be adjusted or maintained. Other fluid flow characteristics can be adjusted or generated with the method 300 by, for example, pulsing the aspiration and/or irrigation.

Because fluid flow through the treatment site created by the method 300 is generally from the first medical instrument towards the second medical instrument, the method 300 is capable of achieving many of the advantages and benefits of directed fluidics previously described. For example, the method 300 can be used to keep a field of view clear, draw the stone (or fragments thereof) towards the second medical instrument for aspiration, hold the stone (or fragments thereof) in place during lithotripsy, and/or permit movement or relocation of the stone (or fragments thereof) by holding the stone to the distal end of the second medical instrument.

The method 300 can include additional steps or blocks not illustrated in FIG. 22A. For example, the method 300 can include determining a characteristic of the treatment site. The characteristic of the treatment site can be, for example, a volume of fluid within the treatment site or a pressure within the treatment site. The determined characteristic of the treatment site can be determined with a sensor or can be calculated based on one or more characteristics of the irrigation and/or aspiration. In some embodiments, the determined characteristic of the treatment site is internal pressure of the treatment site, which can be determined based on irrigation and aspiration pressure and/or irrigation and aspiration flow rate.

In some instances, the determined characteristic of the treatment site can be compared to a threshold value. Upon determination that the determined characteristic meets or exceeds the threshold value, the method can include at least one of reducing irrigation into the treatment site, increasing aspiration from the treatment site, and providing an alert. For example, if the internal pressure of the treatment site is determined to be too high, the irrigation can be decreased and/or the aspiration can be increased in order to lower the pressure within the treatment site. An alarm can also be provided to the physician.

The method 300 may also include the step of moving a distal tip of the first medical instrument and/or the second medical instrument in a sweeping motion while providing irrigation or aspiration. That is, distal tip of the first medical instrument and/or the second medical instrument can be moved in a dithering motion.

The method 300 can also include performing lithotripsy on an object within the treatment site to break the object into fragments. Lithotripsy can be performed with a lithotripter inserted through the first or second medical instruments. The method 300 can also include aspirating the fragments of the object through the second fluid channel of the second medical instrument. In some instances, the second medical instrument is navigated around the treatment site to collect the fragments. In some instances, the fluid flow from the first medical instrument towards the second medical instruments carries the fragments to the second medical instrument for aspiration.

As noted previously, the second medical instrument can be a steerable medical instrument comprising an articulable distal end. The method 300 can include contacting the distal end to an object within the treatment site. Contacting the distal end can include articulating or navigating the distal end to the object. Contacting the distal end to the object can include drawing the object to the distal end with fluid flow. The method 300 can also include providing aspiration through the second fluid channel to hold the object to the distal end of the second medical instrument. The distal end can include a pocket configured to hold the object. The method 300 can further include performing lithotripsy while the object is held to the distal end of the second medical instrument. The method 300 can further include moving the second medical instrument, while the object is held to the distal end, to reposition the object within the treatment site.

In addition to providing irrigation through the first medical instrument at block 306 and aspiration through the second medical instrument 308, the method 300 may also include providing irrigation through the second medical instrument. The second medical instrument can include one or more additional fluid channels for providing irrigation, in addition to the second fluid channel for providing aspiration. See, for example, the device of FIGS. 26A, and 26B.

Figure 22B:
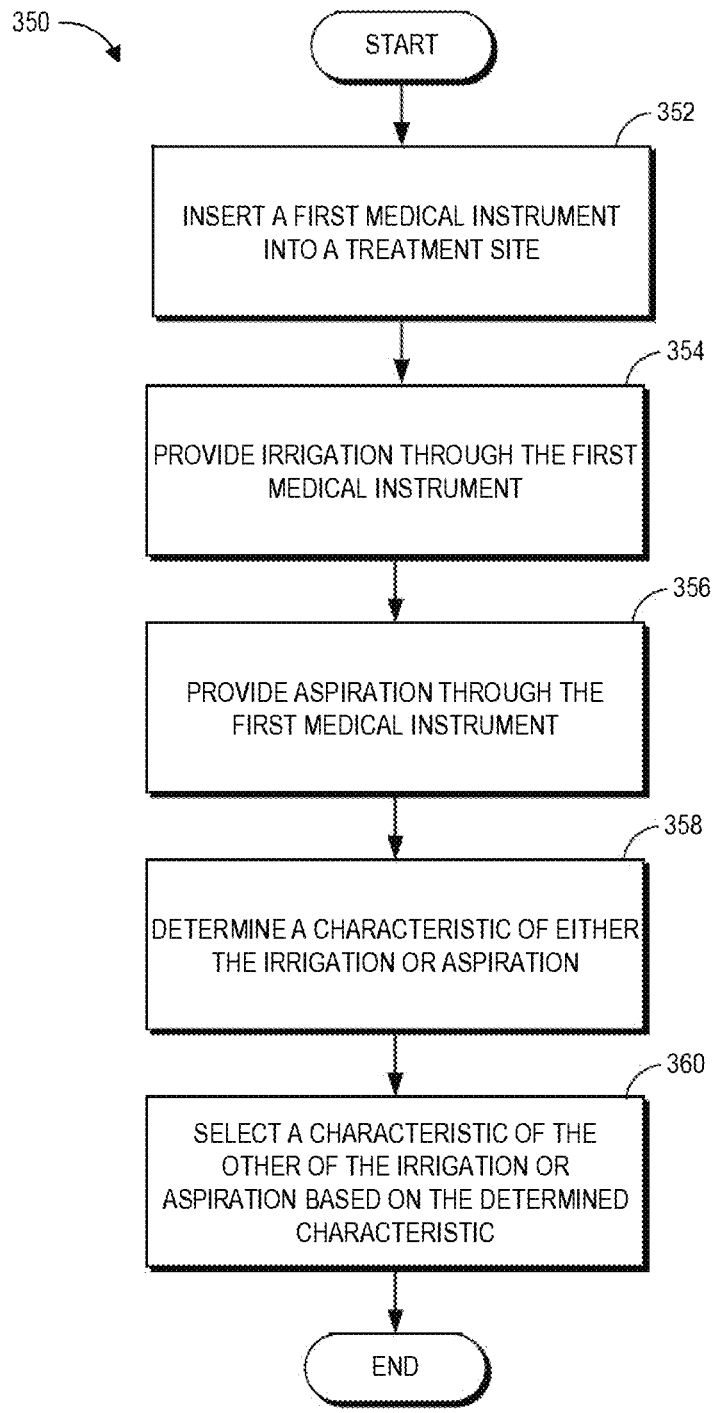
FIG. 22B is a flowchart illustrating an embodiment of another method for directed fluidics during an object removal procedure.

FIG. 22B is a flowchart illustrating an embodiment of another method 350 for administering directed fluidics during a medical procedure, such as an object removal procedure. In some examples, the object removal procedure is a procedure for removing a kidney stone from a kidney. The method 350 can be also be implemented in other types of medical procedures and in other treatment sites. In some embodiments, the method 350 is implemented in a robotic medical system, for example, any of the systems described above with reference to FIGS. 1-15.

In the method 350, both irrigation and aspiration are provided through a single medical instrument, for example, as described above, for example, with reference to FIG. 21B. The medical instrument can be similar to the medical instrument 700 described below with reference to FIGS. 26A and 26B.

The method 350 begins at block 350. At block 352, a first medical instrument is inserted into a treatment site. The first medical instrument can be inserted through a lumen of the patient. In the example of kidney stone removal, the patient lumen may be the ureter. In some examples, the first medical instrument can be inserted percutaneously into the treatment site. The first medical instrument can be an endoscope, nephroscope, catheter, or other type of medical instrument. The first medical instrument can be articulable. In some examples, the first medical instrument is not articulable. In some embodiments, the first medical instrument can include one or more working channels configured to receive various tools (e.g., lithotripters, basket retrieval devices, forceps, etc.) therethrough. The first medical instrument can include at least one first fluid channel and at least one second fluid channel. The first fluid channel and the second fluid channel can be configured to provide fluidics to the treatment site during the medical procedure. In some instances, the distal end of the first medical instrument can be brought into contact with the object to be removed.

At block 354, irrigation is provided through the first medical instrument. For example, irrigation can be provided through the first fluid channel of the first medical instrument. The first fluid channel can be connected to an irrigation source as described above.

At block 356, aspiration is provided through the first medical instrument. For example, aspiration can be provided through the second fluid channel of the first medical instrument. The second fluid channel can be connected to a collection container through a vacuum as described above. In some instances, the order of block 354 and block 356 can be reversed. In some instances, block 354 and block 356 can be performed at the same time. In some instances, block 354 and block 356 can be performed alternatingly, such that irrigation is provided, followed by aspiration, in a series of repetitive steps, for example.

At block 358, the method 350 determines a characteristic of either the irrigation or the aspiration as described above. At block 360, the method 350 selects (e.g., sets or adjusts) a characteristic of the other of the irrigation or aspiration based on the characteristic of the irrigation or aspiration determined at block 358.

Figure 26A:
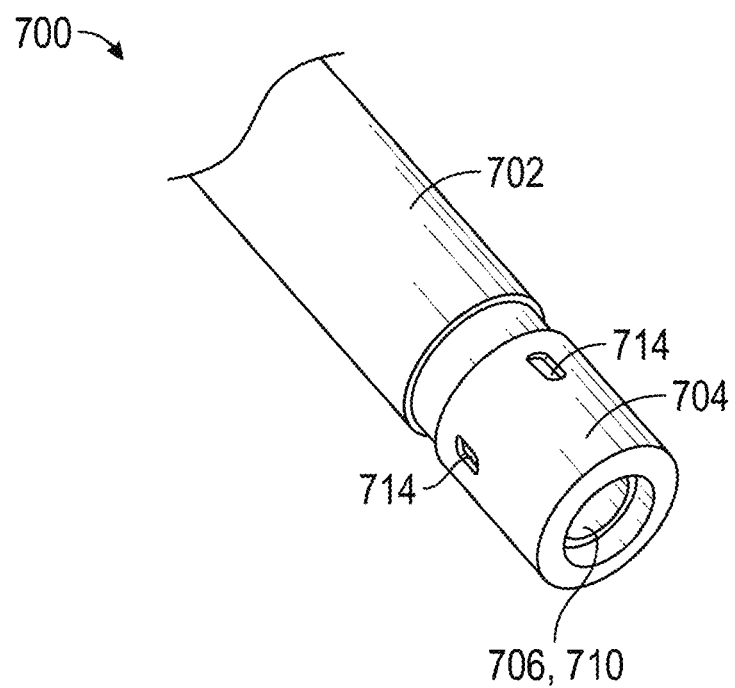
FIG. 26A is a perspective view of a distal end of a medical instrument configured to provide aspiration and irrigation during an object removal procedure.
Figure 26B:
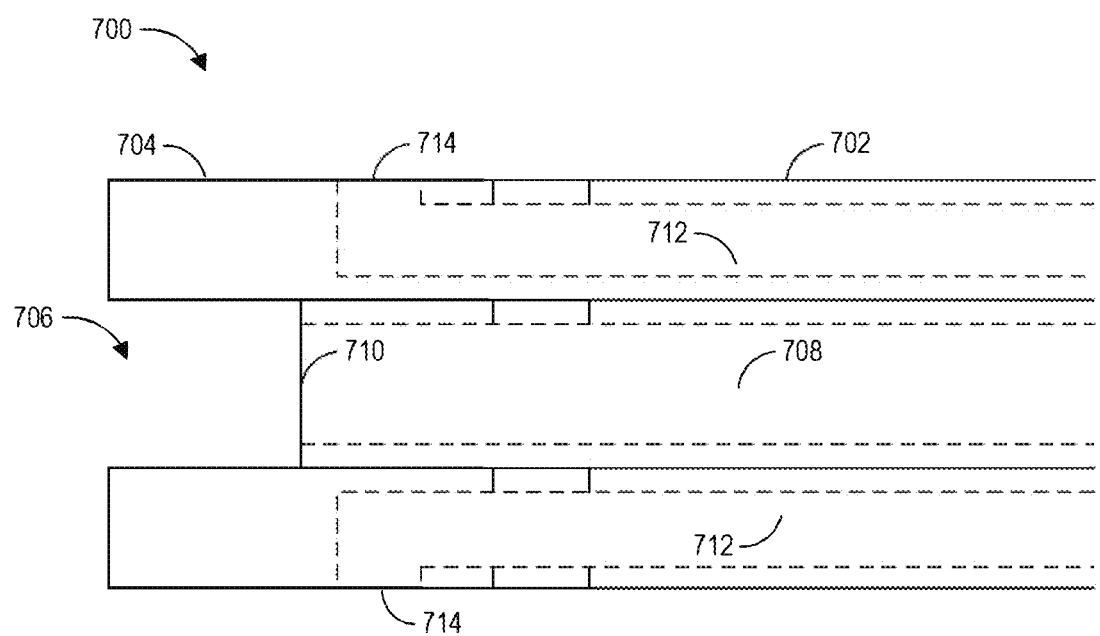
FIG. 26B is a cross-sectional view of the distal end of the medical instrument of FIG. 26A, illustrating the irrigation and aspiration channels within the medical instrument.

The method 350 illustrates that in some examples, directed fluidics can be provided through a single medical instrument, such as the instrument shown in FIGS. 26A and 26B. In some embodiments, a second medical instrument can also be employed during the procedure to perform other tasks, as described above. For example, a second instrument can be a ureteroscope, through which a lithotripter can be deployed for breaking up the object to be removed.

Figure 23:
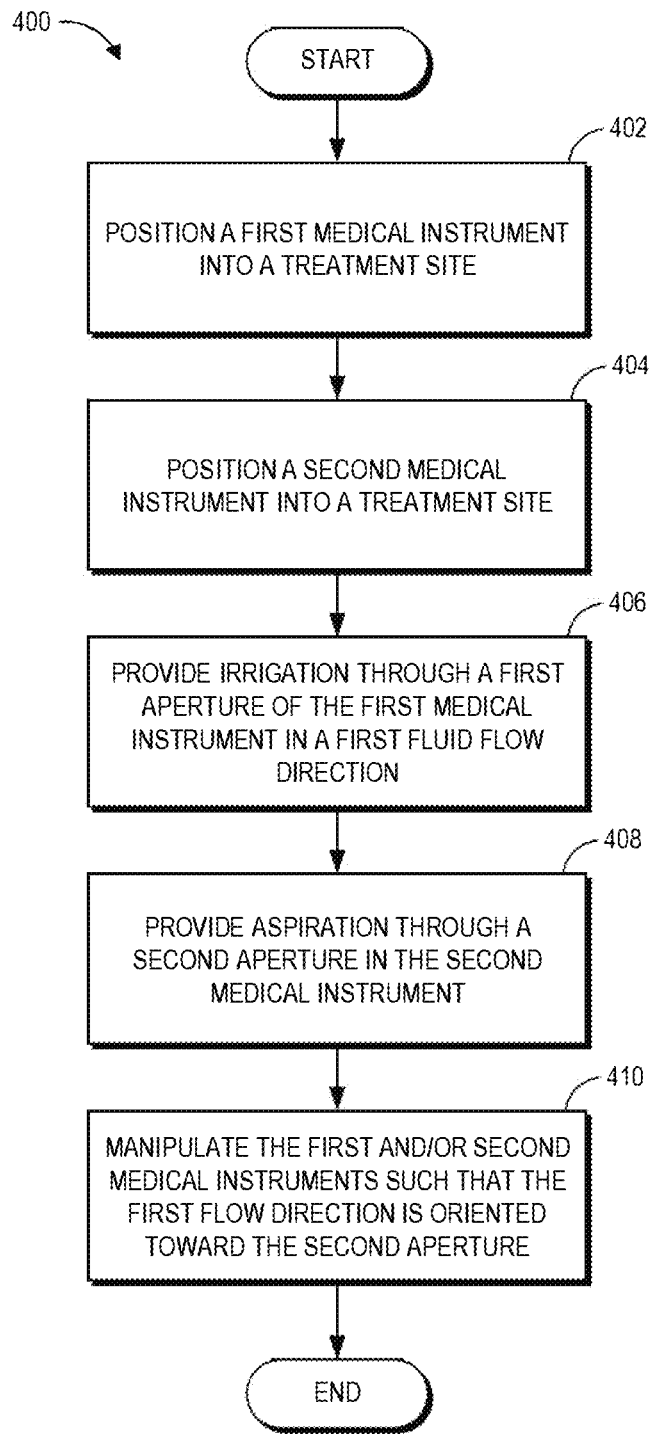
FIG. 23 is a flowchart illustrating an embodiment of another method for directed fluidics during an object removal procedure.

FIG. 23 provides a flowchart illustrating an embodiment of another method 400 for directed fluidics during a medical procedure, such as an object removal procedure. In some examples, the object removal procedure is a procedure for removing a kidney stone from a kidney. The method 400 can be also be implemented in other types of medical procedures and in other treatment sites. In some embodiments, the method 400 is implemented in a robotic medical system, such as any of the systems described above with reference to FIGS. 1-15. In some instances, the method 400 can be performed together with the method 300 of FIG. 22A and/or the method 350 of FIG. 22B.

The method 400 begins at block 402. At block 402, a first medical instrument is positioned into a treatment site. The first medical instrument can be inserted through a lumen of the patient. In the example of kidney stone removal, the patient lumen may be the ureter. In some examples, the first medical instrument can be inserted percutaneously into the treatment site. The first medical instrument can be an endoscope, nephroscope, catheter, or other type of medical instrument. The first medical instrument can be articulable. In some examples, the first medical instrument is not articulable. In some embodiments, the first medical instrument can include one or more working channels configured to receive various tools (e.g., lithotripters, basketing devices, forceps, etc.) therethrough. The first medical instrument can include at least one first fluid channel. The first fluid channel can be configured to provide fluidics to the treatment site during the medical procedure.

At block 404, a second medical instrument is positioned into a treatment site. The second medical instrument can be inserted through a lumen of the patient. In the example of kidney stone removal, the patient lumen may be the ureter. In some examples, the second medical instrument can be inserted percutaneously into the treatment site. The second medical instrument can be an endoscope, nephroscope, catheter, or other type of medical instrument. The second medical instrument can be articulable. In some examples, the second medical instrument is not articulable. The second medical instrument can include one or more working channels configured to receive various tools (e.g., lithotripters, basket retrieval devices, forceps, etc.) therethrough. The second medical instrument can include at least one second fluid channel. The second fluid channel can be configured to provide fluidics to the treatment site during the medical procedure.

In some instances, the order of block 402 and block 404 can be reversed. In some instances, block 402 and block 404 can be performed at the same time.

In some instances, the first and second medical devices are positioned into the treatment site via different methods of access. For example, the first medical instrument may be inserted through a patient lumen and the second medical instrument may be inserted percutaneously, or vice versa. As another example, the first medical instrument can be inserted into the treatment site through a first patient lumen, and the second medical instrument can be inserted into the treatment side through a second patient lumen different than the first patient lumen. As another example, the first medical device can be inserted through a first percutaneous access, and the second medical device can be inserted through a second percutaneous access different than the first percutaneous access. In some examples, the first and second medical devices are inserted through the same patient lumen or through the same percutaneous access.

In some instances, the first and second medical devices are positioned into the treatment site such that the distal ends of the first and second medical devices are separated within the treatment site. For example, the distal end of the first medical device can be positioned antegrade of the object to be removed, and the distal end of the second medical device can be positioned retrograde of the object to be removed. As another example, the distal end of the first medical device can be positioned retrograde of the object to be removed, and the distal end of the second medical device can be positioned antegrade of the object to be removed. In some instances, the first and second medical devices are positioned such that the object is positioned between the distal ends of the first and second medical devices.

At block 406, irrigation is provided through a first aperture of the first medical instrument in a first fluid flow direction. The first fluid flow direction can be, in some embodiments, a direction normal to the first aperture. The first fluid flow direction can be a general flow direction of fluid exiting the first fluid aperture. At block 408, aspiration is provided through a second aperture in the second medical instrument. In some instances, the order of block 406 and block 408 can be reversed. In some instances, block 406 and block 408 can be performed at the same time.

At block 410, the first and/or second medical instruments are manipulated such that the first flow direction is oriented toward the second aperture of the second medical instrument. Manipulating the first and/or second medical instruments can include manipulating the first and/or second medical instruments remotely and/or robotically. Manipulating the first and/or second medical instruments can include moving the first and/or second medical instruments such that the first fluid flow direction is oriented towards or pointed at the second fluid aperture.

According to the method 400, the fluid flow is oriented from the first medical instrument toward the second medical instrument, which can provide one or more of the benefits described above.

The method 400 can include one or more additional steps. For example, the method 400 can include determining the position and/or orientation of the distal ends of the first and/or second medical instruments. The first and/or second medical instruments can include position sensors on the distal ends thereof. The position sensors can be EM sensors. The EM sensors can be configured to provide position information regarding the distal ends of the first and second medical devices as well as orientation information regarding the distal ends of the first and second medical instruments. Other types of position and orientation sensors, such as a shape sensing fiber, for example, can be used. An output of the position sensors can be used to orient the first and second medical instruments.

In some implementations of the method 400, block 410 occurs automatically. For example, the positions and orientations of the distal ends of the first and second medical instruments can be determined, and the first and second medical instruments can be automatically manipulated. For example, the orientation of first medical instrument can be automatically manipulated so as to track the position of the second medical instrument. That is, as the second medical instrument moves, the orientation of the first medical instrument is automatically adjusted such that the first fluid flow direction remains pointed at or oriented toward the second medical instrument. This can help ensure that the fluid flow remains oriented in the proper direction.

Figure 24:
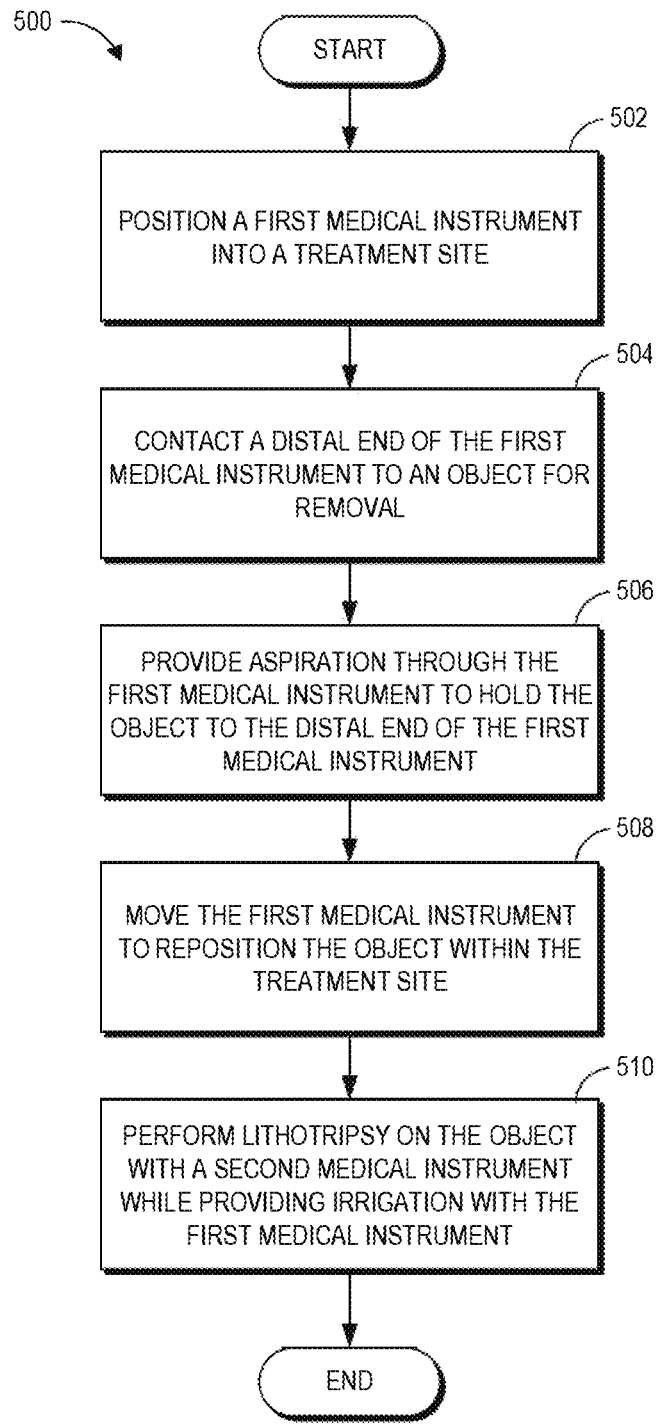
FIG. 24 is a flowchart illustrating an embodiment of a method for holding and repositioning an object using directed fluidics during an object removal procedure.

FIG. 24 is a flowchart illustrating an embodiment of a method 500 for holding and repositioning an object using directed fluidics during a medical procedure, such as an object removal procedure. In some examples, the object removal procedure is a procedure for removing a kidney stone from a kidney. The method 500 can be also be implemented in other types of medical procedures and in other treatment sites. In some embodiments, the method 500 is implemented in a robotic medical system, such as any of the systems described above with reference to FIGS. 1-15. In some instances, the method 500 can be performed together with the method 300 of FIG. 22A, the method 350 of FIG. 22B, and/or the method 400 of FIG. 23. In some instances, the method 500 can be employed using the medical instrument of FIGS. 26A and 26B.

The method 500 begins at block 502. At block 502, a first medical instrument is positioned into a treatment site. For example, the first medical instrument can be inserted through a lumen of the patient. In the example of kidney stone removal, the patient lumen may be the ureter. In some examples, the first medical instrument can be inserted percutaneously into the treatment site. The first medical instrument can be an endoscope, nephroscope, catheter, or other type of medical instrument. The first medical instrument can be articulable. In some examples, the first medical instrument is not articulable. In some embodiments, the first medical instrument can include one or more working channels configured to receive various tools (e.g., lithotripters, basket retrieval devices, forceps, etc.) therethrough. The first medical instrument can include at least one first fluid channel. The first fluid channel can be configured to provide fluidics to or from the treatment site during the medical procedure.

At block 504, a distal end of the first medical instrument is brought into contact with the object to be removed. Contacting the distal end to the object can include articulating or navigating the distal end to the object. In some instances, articulation or navigation of the first medical instrument is achieved robotically, for example, through manipulation of the first medical instrument with an instrument device manipulator or robotic arm to which the first medical instrument is attached. In some instances, articulation or guidance is controlled by a physician controlling the robotic system. In some instances, articulation or guidance is automatically determined by the robotic system. For example, the robotic system can determine the position of the object and the first medical instrument and navigate the first medical instrument to the object. Contacting the distal end to the object can include drawing the object to the distal end with fluid flow, for example with aspiration through the first medical instrument and/or irrigation provided through a second medical instrument.

At block 506, aspiration is provided through the first medical instrument to hold the object to the distal end of the first medical instrument. Aspiration can be provided with a vacuum connected to the first medical instrument. The vacuum can be configured to apply a negative pressure that draws the fluid from the treatment site, through the first medical instrument. In another example, the vacuum can be replaced with a pump, such as peristaltic pump. The pump can be used to move fluid from the treatment site, through the first medical instrument. As fluid is aspirated through the first medical instrument, the fluid flow can hold the object to the distal end of the first medical instrument. In some instances, the first medical instrument can include a pocket (or other receptacle or holding device) on the distal end thereof to help secure the object. See, for example, FIGS. 26A and 26B.

At block 508, the first medical instrument is moved within the treatment site to reposition the object. During movement, aspiration can be maintained to hold the object to the distal end. Movement can be accomplished robotically. Movement can be automatic (e.g., following a preprogramed motion or moving to a preprogramed position) or based on physician input or control. In some instances, the first medical instrument is used to move the object to a location within the treatment site better suited for lithotripsy. For example, the object can be moved to a location where the fragments can more easily be collected or where there is more space in which to work. As another example, the object can be moved away from sensitive regions of the patient's anatomy. In some embodiments, block 508 can be omitted. That is, in some embodiments, the object need not be repositioned within the treatment site.

At block 510, lithotripsy is performed on the object with a second medical instrument while providing irrigation with the second medical instrument. Further, lithotripsy can be performed while the object is held to the distal end of the first medical instrument. The fluid flow from the second medical instrument to the first medical instrument can serve to hold the object during lithotripsy as well as to direct fragments and dust into the first fluid instrument for aspiration and removal. The fluid flow can also maintain a clear visual field which can assist the physician in performing the procedure.

The method 500 can include one or more additional steps. For example, the method 500 can include providing irrigation through the first medical instrument. The first medical instrument may include one or more additional fluid channels (in addition to a first fluid channel for providing aspiration) for providing irrigation. The additional fluid channels may be arranged, for example, as shown in the device of FIGS. 26A and 26B described below. The outflow of irrigation can be oriented away (e.g., radially away) from the distal end of the first medical instrument.

D. Example Systems and Devices for Directed Fluidics.

Figure 25:
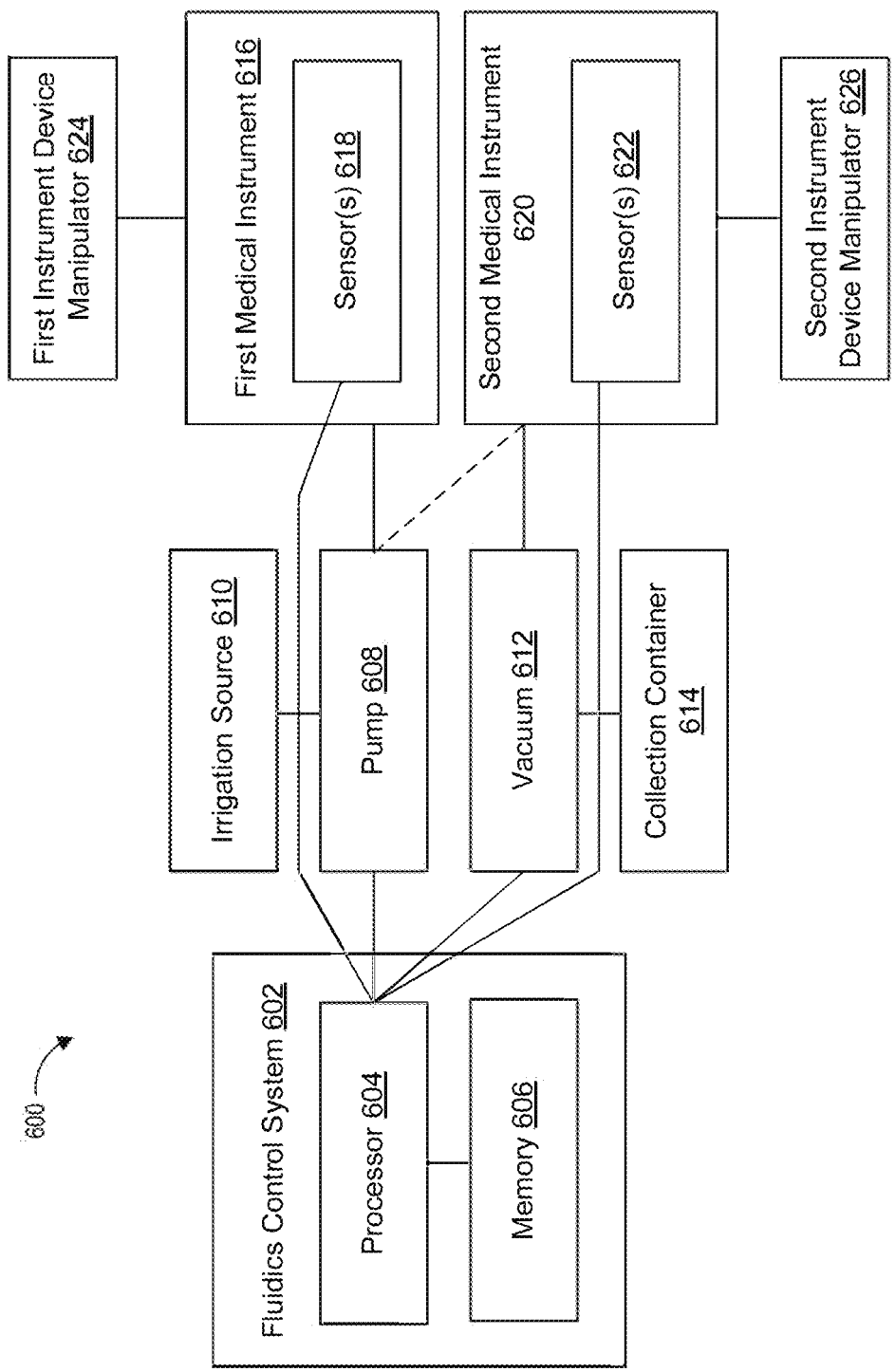
FIG. 25 is a block diagram illustrating an embodiment of a system for directed fluidics.

FIG. 25 is a block diagram illustrating an embodiment of a system 600 for employing directed fluidics during a medical procedure, such as an object removal procedure. In some instances, the methods 300, 400, 500 described above can be implemented using the system 600. Additionally, the system 600 may form part of any of the robotic systems described above with reference to FIGS. 1-15.

As illustrated, the system 600 includes a first medical instrument 616, a second medical instrument 620, a pump 608 connected to the first medical instrument 616, a vacuum 612 connected to the second medical instrument 620, and a directed fluidics module or fluidics control system 602 connected to the pump 608 and the vacuum 612. The directed fluidics control system 602 can be configured to control the pump 608 and the vacuum 612 to provide directed fluidics (e.g., irrigation and aspiration) to the treatment site through the first and second medical instruments 616, 620.

The first medical instrument 616 can be configured to be inserted into the treatment site via a patient lumen. Alternatively, the first medical instrument 616 can be configured to be inserted into the treatment site percutaneously. The first medical instrument 616 can be an endoscope (such as a ureteroscope), a catheter (such as a steerable or non-steerable catheter), a nephroscope, or other type of medical instrument as described herein. The first medical instrument 616 can include a first fluid channel for providing fluidics (irrigation or aspiration). In the illustrated embodiment, the first medical instrument is attached to the pump 608 for providing irrigation. The pump 608 is attached to an irrigation source 610, which provides irrigant (e.g., a saline solution) to be pumped through the first medical instrument and into the treatment site. In some examples, the pump 608 is a peristaltic pump. In some embodiments, the pump 608 can be replaced with a vacuum which applies a vacuum pressure to draw the irrigant from the irrigation source 610 and out through the first medical instrument 616.

The first medical instrument 616 can be connected to a first instrument device manipulator 624. The first instrument device manipulator 624 can be robotically controlled to manipulate the first medical instrument 616. For example, the first medical instrument 616 can be articulable or steerable, and the first instrument device manipulator 624 can be used to articulate or steer the first medical instrument. Further, the first medical device manipulator 624 can be attached to a robotic arm that is configured to insert or retract the first medical device 616 into or out of the treatment site. Examples of instrument device manipulators are described above with reference to FIGS. 1-15. The first medical device 616 can include one or more working channels through which additional tools, such as lithotripters, basket retrieval devices, forceps, etc., can be introduced into the treatment site.

The second medical instrument 620 can be configured to be inserted into the treatment site via a percutaneous access. Alternatively, the second medical instrument 620 can be configured to be inserted into the treatment site via a patient lumen. The second medical instrument 620 can be an endoscope (such as a ureteroscope), a catheter (such as a steerable or non-steerable catheter), a nephroscope, or other type of medical instrument as described herein. The second medical instrument 620 can include a second fluid channel for providing fluidics (irrigation or aspiration). In the illustrated embodiment, the second medical instrument is attached to the vacuum 612 for providing aspiration. The vacuum 612 can be configured to apply a negative pressure to draw fluid out of the treatment site. The vacuum 612 is connected to a collection container into which withdrawn fluid is collected. In some examples, the vacuum 612 can be replaced with a pump which pumps liquid from the treatment site, through the second medical instrument 620, and into the collection container 614.

The second medical instrument 620 can be connected to a second instrument device manipulator 626. The second instrument device manipulator 626 can be robotically controlled to manipulate the second medical instrument 620. For example, the second medical instrument 620 can be articulable or steerable, and the second instrument device manipulator 626 can be configured to articulate or steer the second medical instrument 620. Further, the second medical device manipulator 626 can be attached to a robotic arm that is configured to insert or retract the second medical device 620 into or out of the treatment site. The second medical device 620 can include one or more working channels through which additional tools, such as lithotripters, basket retrieval devices, forceps, etc., can be introduced into the treatment site.

In some embodiments, fluidics are provided through only one of the first medical instrument 616 or the second medical instrument 620, with the instrument providing both irrigation in aspiration. The instrument providing fluidics can be inserted percutaneously into the patient. In some embodiments, the instrument can be similar to the instrument shown in FIGS. 26A and 26B. The other of the first medical instrument 616 or the second medical instrument 620 may not provide fluidics and may be used for other functionality, such as breaking up the object to be removed.

The fluidics control system 602 may include a processor 604 and a memory 606. The memory 606 can include instructions that configure the processor 604 to determine a characteristic of one of the irrigation and the aspiration, and control a characteristic of at least one of the pump or the vacuum based on the determined characteristic. The determined characteristic can be, for example, an instantaneous flow rate of the irrigation or aspiration. The characteristic can be an average flow rate of the irrigation or aspiration over a time interval. The time interval can be, for example, 1.0 seconds, 2.5, second, 5 second, 10 second, 15 seconds or longer, as well as intervals above and below the listed values. The characteristic can be a volume of fluid irrigated or aspirated during a time interval, such as, for example, any of the time intervals listed above. The characteristic can be an instantaneous fluid pressure associated with the irrigation or aspiration. The characteristic can be an average fluid pressure associated with the irrigation or aspirations over a time interval, such as, for example, any of the time intervals listed above. The fluid pressure can be, for example, a fluid pressure within the first fluid channel, a fluid pressure within the second fluid channel, or a fluid pressure within the treatment site itself.

In some instances, the characteristic is determined using one or more sensors, such as the sensors 618, 622 on the first and second medical instruments 616, 620, respectively. The sensor 618 can be positioned, for example, in a first fluid channel of the first medical instrument 616 or on the first medical instrument 616 itself. The sensor 622 can be positioned in a second fluid channel of the second medical instrument 620 or on the second medical instrument 620 itself. In some embodiments, one or both of the first and second medical instruments 616, 620 includes a plurality of sensors 616, 622. The sensors 618, 622 can be flow rate sensors, pressure sensors, or other sensors for determining a characteristic of the irrigation or aspiration. An output from the sensors 616, 622 can be connected to the processor 604, such that the processor 604 can use the output of the sensors 618, 622 to determine the characteristic. In some instances, the characteristic is determined from the pump 608 or vacuum 612 supplying the irrigation or aspiration. For example, the characteristic can be determined based on a flow rate set by the pump 608 or a vacuum pressure applied by the vacuum 612. In some instances, the characteristic is calculated from one or more known or measured parameters. For example, the characteristic can comprise volume of irrigant within the treatment site calculated based on the amount of irrigant pumped into and/or aspirated from the treatment site.

In some embodiments, the sensors 618, 622 comprise position sensors configured to provide positional information regarding the first and second medical instruments 616, 620. The position sensors can provide 3-degree of freedom position information (e.g., x, y, and z coordinates) or 6-degree of freedom position information (e.g., x, y, and z coordinate and pitch, roll, and yaw angles). The position sensors 618, 622 can be for example, EM sensors, shape sensing fibers, or other types of position sensors, including accelerometers, gyroscopes, etc.

In some embodiments, the memory 606 includes instructions that further configure the processor 604 to calculate a position of a first position sensor to determine a position of the first medical instrument 616, calculate a position of s second position sensor to determine a position of the second medical instrument 620, and manipulate the first or second medical instruments 616, 620 such that an outflow aperture of the first medical instrument 616 oriented towards an inflow aperture of the second medical instrument 620.

One or both of the first and second medical instruments 616, 620 can be configured to provide both irrigation and aspiration. For example, as illustrated in FIG. 25, the second medical instrument 620 can be connected to the vacuum 612 for providing aspiration and may also be connected to the pump 608 (via the dotted line) to provide irrigation. In this embodiment, the second medical instrument 620 can include an additional fluid channel for providing irrigation. An example of a medical instrument 700 including a first fluid channel for providing aspiration or irrigation and an additional fluid channel for providing the other of aspiration or irrigation is shown in FIGS. 26A and 26B below.

FIGS. 26A and 26B are perspective and cross-sectional views of a distal end of a medical instrument 700 configured to provide aspiration and irrigation during an object removal procedure. The medical instrument 700 can be used as any of the first and/or second medical instruments described above. The medical instrument 700 can be inserted into the treatment site percutaneously or through a patient lumen.

With reference to FIGS. 26A and 26B, the medical device 700 can include an elongate body 702 that terminates at a distal end 704. In the illustrated embodiment, a pocket 706 or recess is formed in a distal face of the distal end. The pocket 706 provides a space into which an object to be removed can be received during the procedure. In some embodiments, aspiration and/or irrigation holds the object in the pocket 706. The object can be held in the pocket 706 during lithotripsy in order to stabilize and secure the object. As the object is broken apart through lithotripsy, the fragments and dust can be aspirated through the medical instrument 700.

The medical instrument 700 can include a fluid channel 708 (see FIG. 26B). The fluid channel 708 can terminate at a distal end with a fluid orifice 710. The fluid channel 708 can be used for aspiration or irrigation. In one example, the fluid channel 708 is used for aspiration, and fluid drawn into the fluid channel 708 can be used to hold the object within the pocket 706.

The medical instrument 700 may also include one or more additional channels 712 surrounding the fluid channel 708 (see FIG. 26B). These additional channels 712 can be configured to provide the other of aspiration or irrigation than the fluid channel 708. The additional channels 712 may terminate in orifices 714 near the distal end 704 of the medical instrument. The orifices 714 can be positioned in the radial surface of the medical instrument 700 so as to orient flow through the orifices in a radial direction, as shown, for example, in FIGS. 21A and 21B. In some embodiments, the medical instrument 700 includes four orifices 714. In some embodiments, the orifices 714 direct fluid in a direction that is orthogonal or substantially orthogonal to a longitudinal axis of the medical instrument 700. In some embodiments, the orifices 714 direct fluid in a direction that is non-orthogonal or angled with respect to the longitudinal axis of the medical instrument 700.

The medical instrument 700 can be articulable. For example, the medical instrument can include pull-wires (or other mechanisms) for controlling the shape or pose of the medical instrument 700.

Figure 27:
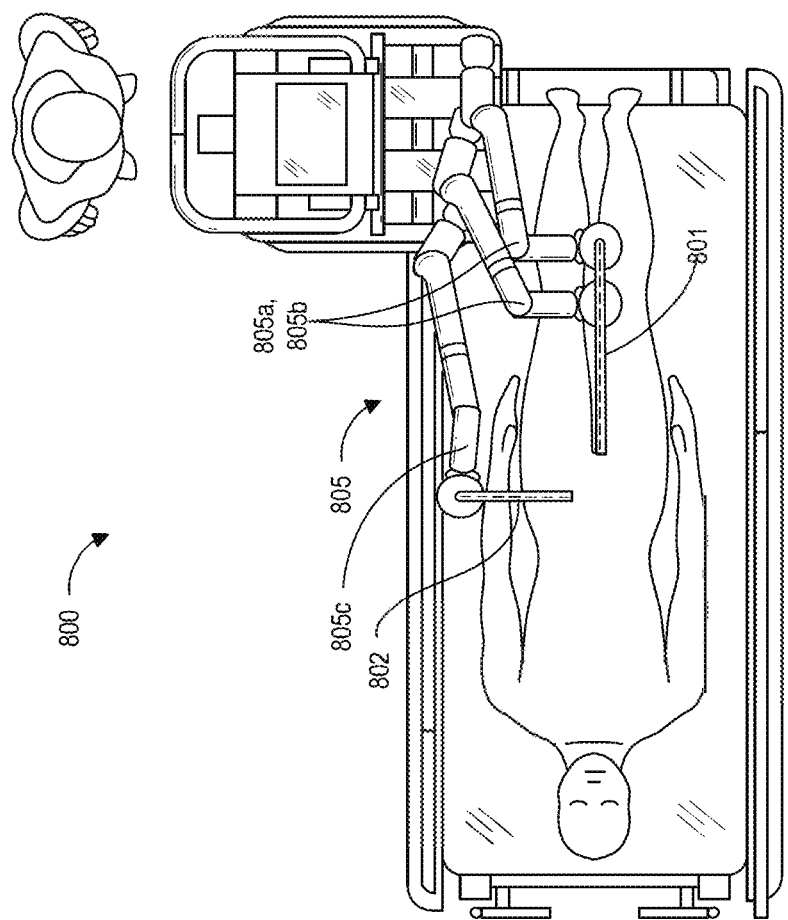
FIG. 27 illustrates an embodiment of a robotic system arranged for performing an object removal procedure using directed fluidics.

FIG. 27 illustrates an embodiment of a robotic system 800 arranged for performing an object removal procedure using directed fluidics. The robotic system 800 may be similar to the robotic systems described above with reference to FIGS. 1-15. In the illustrated embodiment, the robotic system includes a plurality of robotic arms 805. The robotic arms 805 may be configured to manipulate the instruments and tools used during the procedure. As illustrated, the system 800 includes the three robotic arms 805a, 805b, 805c. Other numbers of robotic arms 805 can be used in other embodiments.

The robotic arms 805a, 805b can be attached to a first instrument 801. The first instrument 801 can comprise an outer sheath having a working channel and an inner catheter positioned within the outer sheath. In some embodiments, the robotic arm 805a controls the outer sheath and the robotic arm 805b controls the inner sheath. The first instrument 801 can be inserted into the patient through a patient lumen. As illustrated, the robotic arms 805a, 805b can insert the first instrument 801 into the patient's lower abdomen through the urethra. In some embodiments, insertion is performed along a virtual rail as described above. After insertion into the urethra, using control techniques as described above, the first instrument 801 may be navigated into the treatment site (e.g., the bladder, ureters, and/or kidneys) for diagnostic and/or therapeutic applications.

The robotic arm 805c can be attached to a second instrument 802. In some embodiments, the second instrument 802 can comprise an outer sheath having a working channel and an inner catheter positioned within the outer sheath. In some embodiments, multiple robotic arms can be used to manipulate the second instrument 802. In the illustrated embodiment, the second instrument 802 is inserted percutaneously (i.e., laparoscopically) into the treatment site.

With the first and second instruments 801, 802 positioned by the robotic arms 805 as shown in FIG. 27, the system 800 may be configured to implement directed fluidics as described above. For example, the first and second instruments 801, 802 can be used to provide irrigation and aspiration to the treatment site as described above.

FIG. 27 provides one example of a robotic system 800 configured for directed fluidics. Other systems, including other numbers or types of robotic arms, other numbers or types of medical instruments, and/or other methods for inserting and controlling the instruments are possible.

3. Implementing Systems and Terminology.

Implementations disclosed herein provide systems, methods and apparatuses for removing an object from a treatment site of a patient, and in particular to methods and systems that employ directed fluidics during an object removal procedure. Directed fluidics can include controlling various features of fluid flow (e.g., rate, direction, pressure, etc.) of irrigation and/or aspiration through a treatment site, and/or separating an inflow point of irrigation from an outflow point of aspiration to facilitate an object removal procedure. In some examples, directed fluidics involves controlling a flow direction from an inflow point to an outflow point so as to hold or stabilize an object during the procedure.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases and features used herein referencing specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method of administering fluidics during a medical procedure for removing a kidney stone, the method comprising:
    inserting a first medical instrument percutaneously to a treatment site, the first medical instrument comprising a first fluid channel and a second fluid channel;
    advancing a second medical instrument through a patient lumen to the treatment site, the second medical instrument deploying a lithotripter;
    providing irrigation to the treatment site through the first fluid channel of the first medical instrument;
    holding the kidney stone against the first medical instrument using the irrigation provided through the first fluid channel; and
    breaking up the held kidney stone with the lithotripter deployed by the second medical instrument.

2. The method of claim 1, further comprising:
    determining a position of the kidney stone; and
    navigating a distal end of the first medical instrument towards the determined position of the kidney stone.

3. The method of claim 1, further comprising aspirating fragments of the kidney stone through the second fluid channel to remove the kidney stone.

4. The method of claim 1, further comprising providing aspiration from the treatment site through the second fluid channel of the first medical instrument further comprises:
    determining one or more characteristics of the irrigation provided through the first fluid channel; and
    providing the aspiration from the treatment site through the second fluid channel of the first medical instrument based on the determined one or more characteristics of the irrigation.

5. The method of claim 4, wherein the one or more characteristics of the irrigation include an instantaneous flow rate of the irrigation, an average flow rate of the irrigation over a time interval, a volume of fluid irrigated during a time interval, an instantaneous fluid pressure associated with the irrigation, and an average fluid pressure associated with the irrigation.

6. The method of claim 4, further comprising:
    determining at least one characteristic of the treatment site;
    comparing the determined at least one characteristic of the treatment site to a threshold value; and
    performing at least one of reducing the irrigation into the treatment site and increasing the aspiration from the treatment site based on the comparison.

7. The method of claim 6, wherein the at least one characteristic of the treatment site is determined based on a plurality of sensors located near the treatment site and at least one of one or more characteristics of the irrigation and one or more characteristics of aspiration.

8. The method of claim 1, further comprising:
    determining an orientation of the first medical instrument; and
    automatically adjusting an orientation of the second medical instrument based on the determined orientation of the first instrument.

9. A system for performing a medical procedure to remove a kidney stone, the system comprising:
    a first medical instrument configured to be inserted percutaneously into a treatment site, the first medical instrument includes a first fluid channel and a second fluid channel;
    a second medical instrument configured to be advanced through a patient lumen into the treatment site, the second medical instrument deploying a lithotripter;
    a fluidics control system comprising a processor, wherein the processor is configured to:
        provide irrigation into the treatment site through the first fluid channel of the first medical instrument;
        hold the kidney stone against the first medical instrument using the irrigation provided through the first fluid channel; and
        break up the held kidney stone with the lithotripter deployed by the second medical instrument.

10. The system of claim 9, wherein the processor is further configured to:
    determine a position of the kidney stone; and
    navigate a distal end of the first medical instrument towards the determined position of the kidney stone.

11. The system of claim 9, wherein the processor is further configured to aspirate fragments of the broken kidney stone through the second fluid channel to remove the kidney stone.

12. The system of claim 9, further comprising provide aspiration from the treatment site through the second fluid channel of the first medical instrument further comprises:
    determine at least one characteristic of the irrigation provided through the first fluid channel; and
    provide the aspiration from the treatment site through the second fluid channel of the first medical instrument based on the determined at least one characteristic of the irrigation.

13. The system of claim 12, wherein the at least one characteristic of the irrigation includes an instantaneous flow rate of the irrigation, an average flow rate of the irrigation over a time interval, a volume of fluid irrigated during a time interval, an instantaneous fluid pressure associated with the irrigation, and an average fluid pressure associated with the irrigation.

14. The system of claim 12, wherein the processor is further configured to:
    determine at least one characteristic of the treatment site;
    compare the determined at least one characteristic of the treatment site to a threshold value; and
    perform at least one of reducing the irrigation into the treatment site and increasing the aspiration from the treatment site based on the comparison.

15. The system of claim 14, wherein the at least one characteristic of the treatment site is determined based on a plurality of sensors located near the treatment site and at least one of one or more characteristics of the irrigation and one or more characteristics of aspiration.

16. The system of claim 9, wherein the processor is further configured to:
    determine an orientation of the first instrument; and
    automatically adjust an orientation of the second instrument based on the determined orientation of the first instrument.

17. A medical device to remove a kidney stone, the medical device comprises:
    an articulable elongate body extending along an axis to a distal end;
    a first fluid channel extending along the axis to provide irrigation into a treatment site; and
    at least one additional fluid channel formed through the articulable elongate body to provide aspiration from the treatment site.

18. The medical device of claim 17, wherein the first fluid channel terminates in a first fluid orifice formed in a distal face of the distal end, and wherein the at least one additional fluid channel terminates in at least one additional fluid exit orifice formed in a radical surface of the articulable elongate body proximal the distal end.

19. The medical device of claim 17, further comprising a pocket formed in a face of the distal end, wherein the pocket is configured to at least partially receive the kidney stone to be removed during a medical procedure.

20. The medical device of claim 17, wherein the at least one additional fluid channel annularly surrounds the first fluid channel.

* * * * *